US008222002B2

(12) United States Patent
Sugimura et al.

(10) Patent No.: US 8,222,002 B2
(45) Date of Patent: Jul. 17, 2012

(54) HUMAN ANTI-AMYLOID BETA PEPTIDE ANTIBODY AND FRAGMENT OF SAID ANTIBODY

(75) Inventors: Kazuhisa Sugimura, Kagoshima (JP); Toshihiro Nakashima, Kikuchi (JP)

(73) Assignee: Juridical Foundation The Chemo-Sero-Therapeuric Research Institute, Kumamoto-shi (JP)

( * ) Notice: Subject to any disclaimer, the term of this patent is extended or adjusted under 35 U.S.C. 154(b) by 220 days.

(21) Appl. No.: 12/792,064

(22) Filed: Jun. 2, 2010

(65) Prior Publication Data

US 2010/0267816 A1 Oct. 21, 2010

Related U.S. Application Data

(62) Division of application No. 11/579,072, filed as application No. PCT/JP2005/007628 on Apr. 21, 2005, now Pat. No. 7,763,249.

(30) Foreign Application Priority Data

| Apr. 27, 2004 | (JP) | 2004-131839 |
| Oct. 14, 2004 | (JP) | 2004-300590 |
| Nov. 29, 2004 | (JP) | 2004-343945 |

(51) Int. Cl.
*C12P 21/02* (2006.01)
*C12N 5/10* (2006.01)
*C12N 15/00* (2006.01)
*C12N 15/13* (2006.01)
*C07H 21/04* (2006.01)

(52) U.S. Cl. .......... 435/69.6; 536/23.53; 435/344.1; 435/326; 435/328; 435/320.1; 435/455

(58) Field of Classification Search .................. None
See application file for complete search history.

(56) References Cited

U.S. PATENT DOCUMENTS

| 6,743,427 | B1 | 6/2004 | Schenk | |
| 7,569,389 | B2 * | 8/2009 | Feldmann et al. | 435/468 |
| 7,608,693 | B2 * | 10/2009 | Martin et al. | 530/387.9 |
| 7,973,139 | B2 * | 7/2011 | Bell et al. | 530/387.9 |
| 8,101,553 | B1 * | 1/2012 | Kurosawa et al. | 506/26 |
| 2003/0059937 | A1 | 3/2003 | Ruben et al. | |

FOREIGN PATENT DOCUMENTS

| EP | 0 613 007 | 8/1994 |
| WO | 2004044204 | 5/2004 |

OTHER PUBLICATIONS

Terryberry JW, et al., "Autoantibodies in neurodegenerative diseases: antigen-specific frequencier and intrathecal analysis" Neurobiology Aging, 1998; 19(3):205-216.
Rudikoff S., et al., "Single amino acid substitution altering antigen-binding specificity", Proc. Natl. Acad. Sci. USA, 1982; 79(6):1979-1983.
Paul, WE, Fundamental Immunology, Third Edition. Raven Press, New York, 1993, pp. 292-295.
Padlan EA, et al., Structure of an antibody-antigen complex: Crystal structure of the HyHEL-10 Fab-lysozyme complex. Proc Natl. Acad. Sci USA., 1989; 86:5938-5942.
Solomon, Beka, et al., Proc. Natl. Acad. Sci. USA, 93(1), p. 452-455, (1996), "Moncolonal Antibodiesinhibit in Vitro Fibrillar Aggregation of the Alzheimer Beta-Amyloid Peptide".
Schenk, Dale, et al., Nature 400(6740), p. 173-177 (1990), "Immunization with Amyloid-Betaattenuates Alzheimer-Disease-Like Pathology in the PDAPP Mouse".
Nicoll, James. A., et al. Nature Medicine, 9(4), p. 448-452, (2003), "Neuropathology of Human Alzheimer Disease after Immunication with Amyloid-Beta Peptide: A Case Report".
Monsinego, Alon. et al., Science, 302(5646), p. 834,838, (2003) "Immunotherapeutic Approaches to Alzheimer's Disease".
McLaurin, J. et al., Nature Medicine, 8(11), p. 1263-1269, (2002). "Therapeutically Effective Antibodies Against Amyloid-Beta Peptide Target Amyloid-Beta Residues 4-10 and Inhibit Cytitixicity and Fibrillogenesis".
McCafferty, John. et al., Nature, 348(6301), p. 552-554, (1990), "Phage Antibodies: Filamentous Phage Displaying Antibody Variable Domains".
Lei, Shau-Ping. et al., Journal of Bacteriol., p. 4379-4383, (1987), "Characterization of the Erwinia Cartovora Pelb Gene and its Product Pectate Lyase".
Marks, James. D. et al., J. Mol. Biol., 222(3), p. 581-597, (1991), "By-Passing Immunization. Human Antibodies From V-Gene Libraries Displayed on Phage".
Cai. Jiong. et al., Zhongguo Yi xuew Ke xue yuan Xue bao 25(5), p. 557-563, (2003), "Cloning and Expression of Human Single-Chain FV Antibody Against Amyloid Beta Peptide Involved in Alzheimer's Disease".
Frenkel, Dan. et al., Journal of Neuroimmunology, 106(1-2), p. 23-31, (2000), "Modulation of Alzheimer's Beta-Amyloid Neurotoxicity by Site-Directed Single-Chain Antibody".
Manoutcharian K., et al., Journal of Neuroimmunology, 145(1-2), p. 12-17, (2003), "Amyloid-Beta Peptide-Specific Single Chain FV Antibodies Isolated from an Immune Phage display Library".
Owens, Raymond. J. et al., Journal of Immunological Methods, 168(2), p. 149-165, (1994), "The Genetic Engineering of Monoclonal Aantibodies".
Bard, et al., "Epitipe and Isotype Specificities of Antobodies to Beta-Amyloid Peptide for Protection Against Alzheimer's Disease-like Neuropathology," Proceedings of the National Academy of Sciences of USA, 2003, pp. 2023-2028, vol. 100, No. 4, ISSN 0027-8424, National Academy of Science, Washington, DC.
Bard et al., "Peripherally Administered Antibodies Against Amyloid Beta-Peptide Enter the Central Nervous System and Reduce Pathology in a Mouse Model of Alzheimer disease,"Nature Medicine, 2000, pp. 916-919, vol. 6, No. 8, ISSN 1078-8956, Nature Publishing Group, New York, NY.
U.S. Appl. No. 12/792,134, filed Jun. 2, 2010, Sugimura, et al.

\* cited by examiner

*Primary Examiner* — Bridget E Bunner
*Assistant Examiner* — Kimberly A Ballard
(74) *Attorney, Agent, or Firm* — Oblon, Spivak, McClelland, Maier & Neustadt, L.L.P.

(57) ABSTRACT

A human anti-amyloid β peptide (hereinafter referred to as "Aβ") antibody that binds to Aβ to thereby inhibit aggregation of Aβ molecules, and a fragment of said antibody are provided. The antibody and a fragment thereof according to the present invention, comprising a variable region of a human-derived anti-Aβ antibody, strongly reacts with Aβ to thereby inhibit its aggregation and hence may be used as a medicament for the prophylaxis and treatment of Alzheimer dementia.

15 Claims, 9 Drawing Sheets

M;  Marker
lane1;  VL expressed in E. coli recovered from periplasm fraction
lane2;  VL expressed in E. coli recovered from cytoplasm fraction
lane3 and 4;  VL-g3-D1-D2 fusion protein expressed in E.coli recovered from periplasm fraction

SEQUENCE LISTING

```
<160> NUMBER OF SEQ ID NOS: 106

<210> SEQ ID NO 1
<211> LENGTH: 118
<212> TYPE: PRT
<213> ORGANISM: Homo sapiens

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Thr Thr Ala Ser Pro Leu Asp Tyr Trp Gly Gln Gly Thr
            100                 105                 110

Leu Val Thr Val Ser Ser
```

<210> SEQ ID NO 2
<211> LENGTH: 6
<212> TYPE: PRT
<213> ORGANISM: Homo sapiens

<400> SEQUENCE: 2

Ser Ser Tyr Ala Ile Ser
1               5

<210> SEQ ID NO 3
<211> LENGTH: 17
<212> TYPE: PRT
<213> ORGANISM: Homo sapiens

<400> SEQUENCE: 3

Arg Ile Ile Pro Ile Phe Gly Ile Ala Asn Tyr Ala Gln Lys Phe Gln
1               5                   10                  15

Gly

<210> SEQ ID NO 4
<211> LENGTH: 9
<212> TYPE: PRT
<213> ORGANISM: Homo sapiens

<400> SEQUENCE: 4

Gly Thr Thr Ala Ser Pro Leu Asp Tyr
1               5

<210> SEQ ID NO 5
<211> LENGTH: 354
<212> TYPE: DNA
<213> ORGANISM: Homo sapiens

<400> SEQUENCE: 5
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaagg atcatcccta tctttggtat agcaaactac     180
gcacagaagt tccagggcag agtcacgatt accgcggaca atccacgag cacagcctac      240 atggagctga gcagcctgag atctgaggac acggccgtgt attactgtgc gagagggact     300
acggcgagcc cccttgacta ctggggccag ggcaccctgg tcaccgtctc ctca           354

<210> SEQ ID NO 6
<211> LENGTH: 111
<212> TYPE: PRT
<213> ORGANISM: Homo sapiens

<400> SEQUENCE: 6

Leu Pro Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Thr Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Asp Ser Leu Ala Ile Ser Gly Leu Arg
65                  70                  75                  80

```
Ser Glu Asp Glu Ala Asp Tyr Tyr Cys Ala Val Trp Asp Ala Ser Leu
                85                  90                  95

Arg Gly Trp Leu Phe Gly Gly Gly Thr Gln Leu Thr Val Leu Gly
            100                 105                 110

<210> SEQ ID NO 7
<211> LENGTH: 13
<212> TYPE: PRT
<213> ORGANISM: Homo sapiens

<400> SEQUENCE: 7

Ser Gly Ser Ser Ser Asn Ile Gly Thr Asn Tyr Val Tyr
1               5                   10

<210> SEQ ID NO 8
<211> LENGTH: 7
<212> TYPE: PRT
<213> ORGANISM: Homo sapiens

<400> SEQUENCE: 8

Arg Asn Asn Gln Arg Pro Ser
1               5

<210> SEQ ID NO 9
<211> LENGTH: 11
<212> TYPE: PRT
<213> ORGANISM: Homo sapiens

<400> SEQUENCE: 9

Ala Val Trp Asp Ala Ser Leu Arg Gly Trp Leu
1               5                   10

<210> SEQ ID NO 10
<211> LENGTH: 333
<212> TYPE: DNA
<213> ORGANISM: Homo sapiens

<400> SEQUENCE: 10
ctgcctgtgc tgactcagcc cccctcagcg tctgggaccc ccgggcagag ggtcaccatc      60
tcttgttctg gaagcagctc caatatcggc actaattatg tatactggta ccagcagctc     120
ccaggaacgg cccccaaact tctcatctat aggaataatc agcggccctc agggggtccct   180 gaccgattct ctggctccaa gtctggcacc tcagactccc tggccatcag tgggctccgg     240
tccgaggatg aggctgatta ttactgtgca gtatgggatg ccagcctgcg tggttggctg     300
ttcggcggag ggacccagct caccgtttta ggt                                  333

<210> SEQ ID NO 11
<211> LENGTH: 123
<212> TYPE: PRT
<213> ORGANISM: Homo sapiens

<400> SEQUENCE: 11

Glu Val Gln Leu Val Glu Ser Gly Thr Glu Val Lys Lys Pro Gly Glu
1               5                   10                  15

Ser Leu Lys Ile Ser Cys Lys Gly Ser Glu Tyr Arg Phe Ser Ser Tyr
                20                  25                  30

Trp Ile Ala Trp Val Arg Gln Met Pro Gly Lys Gly Leu Asp Trp Met
            35                  40                  45

Gly Leu Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
```

```
                 65                  70                  75                  80
Leu Gln Trp Ser Ser Leu Lys Ala Ser Asp Thr Ala Met Tyr Tyr Cys
                         85                  90                  95

Ala Arg His Gln Leu Arg Gly Ile Ala Ala Arg Ser Pro Phe Asp Ile
                100                 105                 110

Trp Gly Gln Gly Thr Met Val Thr Val Ser Ser
            115                 120

<210> SEQ ID NO 12
<211> LENGTH: 6
<212> TYPE: PRT
<213> ORGANISM: Homo sapiens

<400> SEQUENCE: 12

Ser Ser Tyr Trp Ile Ala
1               5

<210> SEQ ID NO 13
<211> LENGTH: 17
<212> TYPE: PRT
<213> ORGANISM: Homo sapiens

<400> SEQUENCE: 13

Leu Ile Tyr Pro Gly Asp Ser Asp Thr Arg Tyr Ser Pro Ser Phe Gln
1               5                   10                  15

Gly

<210> SEQ ID NO 14
<211> LENGTH: 14
<212> TYPE: PRT
<213> ORGANISM: Homo sapiens

<400> SEQUENCE: 14

His Gln Leu Arg Gly Ile Ala Ala Arg Ser Pro Phe Asp Ile
1               5                   10

<210> SEQ ID NO 15
<211> LENGTH: 369
<212> TYPE: DNA
<213> ORGANISM: Homo sapiens

<400> SEQUENCE: 15
gaggtgcagc tggtggagtc tggaacagag gtgaaaaagc ccggggagtc tctgaagatc    60
tcctgtaagg gttctgaata taggttctcc agctactgga tcgcctgggt gcgccagatg   120
cccgggaaag gcctggactg gatggggctc atctatcctg gtgactctga taccagatac   180
agcccgtcct tccaaggcca ggtcaccatc tcagccgaca gtccatcag caccgcctac   240
ctgcagtgga gcagcctgaa ggcctcggac accgccatgt attactgtgc gaggcaccaa   300
cttaggggta tagcagctcg gtcgcctttt gatatctggg gccaagggac aatggtcacc   360
gtctcttca                                                            369

<210> SEQ ID NO 16
<211> LENGTH: 111
<212> TYPE: PRT
<213> ORGANISM: Homo sapiens

<400> SEQUENCE: 16

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Gly Asp Val Gly Arg Asn
```

```
            20                  25                  30
Asn Tyr Val Ser Trp Tyr Gln His His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ser Thr Ser
                85                  90                  95

Ser Thr Trp Val Phe Gly Gly Gly Thr Lys Leu Thr Val Leu Gly
            100                 105                 110

<210> SEQ ID NO 17
<211> LENGTH: 14
<212> TYPE: PRT
<213> ORGANISM: Homo sapiens

<400> SEQUENCE: 17

Thr Gly Thr Ser Gly Asp Val Gly Arg Asn Asn Tyr Val Ser
1               5                   10

<210> SEQ ID NO 18
<211> LENGTH: 7
<212> TYPE: PRT
<213> ORGANISM: Homo sapiens

<400> SEQUENCE: 18

Asp Val Ser Lys Arg Pro Ser
1               5

<210> SEQ ID NO 19
<211> LENGTH: 10
<212> TYPE: PRT
<213> ORGANISM: Homo sapiens

<400> SEQUENCE: 19

Ser Ser Tyr Thr Ser Ser Ser Thr Trp Val
1               5                   10

<210> SEQ ID NO 20
<211> LENGTH: 333
<212> TYPE: DNA
<213> ORGANISM: Homo sapiens

<400> SEQUENCE: 20
caatctgccc tgactcagcc tccctccgcg tccgggtctc ctggacagtc agtcaccatc      60
tcctgcactg gaaccagcgg tgacgttggt agaaataact atgtctcctg gtaccaacat    120
cacccaggca aagcccccaa actcatgatt tatgatgtca gtaagcggcc ctcaggggtt    180
tctaatcgct tctctggctc caagtctggt aacacggcct ccctgaccat ctctgggctc    240
caggctgagg acgaggctga ttattactgc agctcatata caagcagcag cacttgggtg    300
ttcggcggag ggaccaagct gaccgtccta ggt                                  333

<210> SEQ ID NO 21
<211> LENGTH: 122
<212> TYPE: PRT
<213> ORGANISM: Homo sapiens

<400> SEQUENCE: 21

Gln Val Gln Leu Gln Gln Ser Gly Ala Glu Val Lys Lys Pro Gly Ala
1               5                   10                  15
```

Ser Val Lys Val Ser Cys Lys Ala Ser Gly Tyr Thr Phe Ser Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Arg Tyr Asn Trp Asn Asp Gly Asp Ala Phe Asp Ile Trp
            100                 105                 110

Gly Gln Gly Thr Met Val Thr Val Ser Ser
        115                 120

<210> SEQ ID NO 22
<211> LENGTH: 6
<212> TYPE: PRT
<213> ORGANISM: Homo sapiens

<400> SEQUENCE: 22

Ser Ser Tyr Tyr Met His
1               5

<210> SEQ ID NO 23
<211> LENGTH: 17
<212> TYPE: PRT
<213> ORGANISM: Homo sapiens

<400> SEQUENCE: 23

Ile Ile Asn Pro Ser Gly Gly Ser Thr Ser Tyr Ala Gln Lys Phe Gln
1               5                   10                  15

Gly

<210> SEQ ID NO 24
<211> LENGTH: 13
<212> TYPE: PRT
<213> ORGANISM: Homo sapiens

<400> SEQUENCE: 24

Pro Arg Tyr Asn Trp Asn Asp Gly Asp Ala Phe Asp Ile
1               5                   10

<210> SEQ ID NO 25
<211> LENGTH: 366
<212> TYPE: DNA
<213> ORGANISM: Homo sapiens

<400> SEQUENCE: 25
caggtacagc tgcagcagtc aggggctgag gtgaagaagc ctggggcctc agtgaaggtc      60
tcctgcaagg cttctggata caccttcagc agctactata tgcactgggt gcgacaggcc    120
cctggacaag gcttgagtg gatgggaata atcaaccta gtggtggtag cacaagctac      180
gcacagaagt tccagggcag agtcaccatg accaggaca cgtccacgag cacagtctac     240
atggagctga gcagcctgag atctgaggac acggccgtgt attactgtgc gaggccgcgg    300
tataactgga cgacggtga tgcttttgat atctggggcc aagggacaat ggtcaccgtc     360
tcttca                                                              366

```
<210> SEQ ID NO 26
<211> LENGTH: 110
<212> TYPE: PRT
<213> ORGANISM: Homo sapiens

<400> SEQUENCE: 26

Gln Thr Val Val Thr Gln Glu Pro Ala Val Ser Val Ala Leu Gly Gln
1               5                   10                  15

Thr Val Thr Ile Thr Cys Gln Gly Asp Ser Leu Arg Arg Tyr Tyr Ala
            20                  25                  30

Ser Trp Tyr Gln Gln Lys Pro Gly Gln Ala Pro Val Leu Val Val Tyr
        35                  40                  45

Gly Lys Asn Lys Arg Pro Ser Arg Ile Pro Ala Arg Phe Ser Ala Ser
    50                  55                  60

Ser Ser Arg Asn Thr Ala Ser Leu Thr Ile His Gly Ala Arg Ala Glu
65                  70                  75                  80

Asp Glu Ala Asp Tyr Tyr Cys Glu Ser Arg Asp Ile Ser Gly Asn His
                85                  90                  95

Leu Tyr Val Phe Gly Thr Gly Thr Lys Val Thr Val Leu Gly
            100                 105                 110

<210> SEQ ID NO 27
<211> LENGTH: 11
<212> TYPE: PRT
<213> ORGANISM: Homo sapiens

<400> SEQUENCE: 27

Gln Gly Asp Ser Leu Arg Arg Tyr Tyr Ala Ser
1               5                   10

<210> SEQ ID NO 28
<211> LENGTH: 7
<212> TYPE: PRT
<213> ORGANISM: Homo sapiens

<400> SEQUENCE: 28

Gly Lys Asn Lys Arg Pro Ser
1               5

<210> SEQ ID NO 29
<211> LENGTH: 12
<212> TYPE: PRT
<213> ORGANISM: Homo sapiens

<400> SEQUENCE: 29

Glu Ser Arg Asp Ile Ser Gly Asn His Leu Tyr Val
1               5                   10

<210> SEQ ID NO 30
<211> LENGTH: 330
<212> TYPE: DNA
<213> ORGANISM: Homo sapiens

<400> SEQUENCE: 30
cagactgtgg tgactcagga gcctgctgtg tctgtggcct tgggacagac agtcacgatc      60
acatgccaag agacagtct cagaaggtat tatgcaagtt ggtaccagca gaagccagga     120
caggcccctg ttcttgtcgt ctatggtaaa aacaagcggc cctcaaggat ccagcccga     180 ttctctgcct ccagttcaag aaacacagcc tccttgacca ttcatggggc tcgggcggaa     240
gatgaggctg actattattg tgaatcccgg gacatcagtg gtaatcatct ttatgtcttc     300
ggaactggga ccaaggtcac cgtcctaggt                                      330
```

<210> SEQ ID NO 31
<211> LENGTH: 123
<212> TYPE: PRT
<213> ORGANISM: Homo sapiens

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Ser Ile Ala Ala Arg Pro Trp Tyr Tyr Phe Asp Tyr
            100                 105                 110

Trp Gly Gln Gly Thr Leu Val Thr Val Ser Ser
        115                 120

<210> SEQ ID NO 32
<211> LENGTH: 6
<212> TYPE: PRT
<213> ORGANISM: Homo sapiens

<400> SEQUENCE: 32

Thr Ser Tyr Asp Ile Asn
1               5

<210> SEQ ID NO 33
<211> LENGTH: 17
<212> TYPE: PRT
<213> ORGANISM: Homo sapiens

<400> SEQUENCE: 33

Trp Met Asn Pro Asn Ser Gly Asn Thr Gly Tyr Ala Gln Lys Phe Gln
1               5                   10                  15

Gly

<210> SEQ ID NO 34
<211> LENGTH: 14
<212> TYPE: PRT
<213> ORGANISM: Homo sapiens

<400> SEQUENCE: 34

Gly Arg Ser Ile Ala Ala Arg Pro Trp Tyr Tyr Phe Asp Tyr
1               5                   10

<210> SEQ ID NO 35
<211> LENGTH: 369
<212> TYPE: DNA
<213> ORGANISM: Homo sapiens

<400> SEQUENCE: 35
caggtgcagc tggtgcagtc tggggctgag gtgaagaagc ctggggcctc agtgaaggtc     60
tcctgcaagg cttctggata caccttcacc agttatgata tcaactgggt gcgacaggcc    120

```
actggacaag ggcttgagtg gatgggatgg atgaacccta acagtggtaa cacaggctat    180
gcacagaagt tccagggcag agtcaccatg accaggaaca cctccataag cacagcctac    240
atggagctga gcagcctgag atctgaggac acggccgtgt attactgtgc gagaggccgg    300
agtatagcag ctcgtccctg gtactacttt gactactggg ccagggcac cctggtcacc     360 gtctcctca                                                            369
```

<210> SEQ ID NO 36
<211> LENGTH: 109
<212> TYPE: PRT
<213> ORGANISM: Homo sapiens

<400> SEQUENCE: 36

```
Glu Thr Thr Leu Thr Gln Ser Pro Arg Thr Leu Ser Leu Ser Pro Gly
1               5                   10                  15

Gln Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Arg
    50                  55                  60

Gly Ser Gly Ser Gly Thr Leu Phe Thr Leu Thr Ile Ser Arg Leu Glu
65                  70                  75                  80

Pro Glu Asp Phe Ala Val Tyr Tyr Cys Gln Gln Phe Ser Ser Ser Arg
                85                  90                  95

Tyr Ile Phe Gly Gln Gly Thr Lys Leu Glu Ile Lys Arg
            100                 105
```

<210> SEQ ID NO 37
<211> LENGTH: 12
<212> TYPE: PRT
<213> ORGANISM: Homo sapiens

<400> SEQUENCE: 37

```
Arg Ala Ser Gln Ser Val Ser Ser Ser Tyr Leu Ala
1               5                   10
```

<210> SEQ ID NO 38
<211> LENGTH: 7
<212> TYPE: PRT
<213> ORGANISM: Homo sapiens

<400> SEQUENCE: 38

```
Gly Ala Ser Ser Arg Ala Thr
1               5
```

<210> SEQ ID NO 39
<211> LENGTH: 9
<212> TYPE: PRT
<213> ORGANISM: Homo sapiens

<400> SEQUENCE: 39

```
Gln Gln Phe Ser Ser Ser Arg Tyr Ile
1               5
```

<210> SEQ ID NO 40
<211> LENGTH: 327
<212> TYPE: DNA
<213> ORGANISM: Homo sapiens

<400> SEQUENCE: 40

```
gaaacgacac tcacgcagtc tccacgcacc ctgtctttgt ctccagggca aagagccacc      60
ctctcctgca gggccagtca gagtgttagt agcagctact tagcctggta ccagcagaaa     120
cctggccagg ctcccaggct cctcatctat ggtgcatcca gcagggccac tggcatcccg     180
gacaggttcc gtggcagtgg gtctgggaca ctcttcactc tcaccatcag cagactggag     240
cctgaagatt ttgcagtgta ttactgtcaa cagtttagta gctcacggta catttttggc     300
caggggacca agctggagat caaacgt                                         327
```

```
<210> SEQ ID NO 41
<211> LENGTH: 123
<212> TYPE: PRT
<213> ORGANISM: Homo sapiens

<400> SEQUENCE: 41

Gln Val Gln Leu Val Gln Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Val Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Met Tyr
                85                  90                  95

Tyr Cys Thr Arg Val Arg Ser Gly Ser Tyr Tyr Ala Arg Pro Asp Tyr
            100                 105                 110

Trp Gly Gln Gly Thr Leu Val Thr Val Ser Ser
        115                 120
```

```
<210> SEQ ID NO 42
<211> LENGTH: 6
<212> TYPE: PRT
<213> ORGANISM: Homo sapiens

<400> SEQUENCE: 42

Gly Asp Tyr Ala Met Ser
1               5
```

```
<210> SEQ ID NO 43
<211> LENGTH: 19
<212> TYPE: PRT
<213> ORGANISM: Homo sapiens

<400> SEQUENCE: 43

Phe Ile Arg Ser Lys Ala Tyr Gly Gly Thr Thr Glu Tyr Ala Ala Ser
1               5                   10                  15

Val Lys Gly
```

```
<210> SEQ ID NO 44
<211> LENGTH: 12
<212> TYPE: PRT
<213> ORGANISM: Homo sapiens

<400> SEQUENCE: 44

Val Arg Ser Gly Ser Tyr Tyr Ala Arg Pro Asp Tyr
1               5                   10
```

<210> SEQ ID NO 45
<211> LENGTH: 369
<212> TYPE: DNA
<213> ORGANISM: Homo sapiens

<400> SEQUENCE: 45

```
caggtgcagc tggtgcagtc tgggggaggc ttggtacagc cagggcggtc cctgagactc      60
tcctgtacag cttctggatt cacctttggt gattatgcta tgagctgggt ccgccaggct     120
ccagggaagg ggctggagtg ggtaggtttc attagaagca aagcttatgg tgggacaaca     180
gagtacgccg cgtctgtgaa aggcagattc accatctcaa gagatgattc caaaagcatc     240
gcctatctgc aaatgaacag cctgaaaacc gaggacacag ccatgtatta ctgtactaga     300
gttaggagtg ggagctacta cgcgaggcct gactactggg gccagggaac cctggtcacc     360
gtctcctca                                                             369
```

<210> SEQ ID NO 46
<211> LENGTH: 108
<212> TYPE: PRT
<213> ORGANISM: Homo sapiens

<400> SEQUENCE: 46

Gln Ala Val Leu Thr Gln Pro Ser Gly Thr Pro Gly Gln Arg Val Thr
1               5                   10                  15

Leu Ser Cys Ser Gly Ser Ser Ser Asn Ile Gly Ser Asn Thr Val Tyr
            20                  25                  30

Trp Tyr Arg Gln Leu Pro Gly Thr Ala Pro Arg Leu Leu Ile Tyr Ser
        35                  40                  45

Tyr Asn Gln Arg Pro Ser Gly Val Pro Asp Arg Phe Ser Gly Ser Lys
    50                  55                  60

Ser Gly Thr Ser Ala Ser Leu Ala Ile Ser Gly Leu Arg Ser Glu Asp
65                  70                  75                  80

Glu Ala Asp Tyr Tyr Cys Ala Ala Trp Asp Asp Ser Leu Ser Gly Tyr
                85                  90                  95

Val Phe Gly Thr Gly Thr Lys Val Thr Val Leu Gly
            100                 105

<210> SEQ ID NO 47
<211> LENGTH: 13
<212> TYPE: PRT
<213> ORGANISM: Homo sapiens

<400> SEQUENCE: 47

Ser Gly Ser Ser Ser Asn Ile Gly Ser Asn Thr Val Tyr
1               5                   10

<210> SEQ ID NO 48
<211> LENGTH: 7
<212> TYPE: PRT
<213> ORGANISM: Homo sapiens

<400> SEQUENCE: 48

Ser Tyr Asn Gln Arg Pro Ser
1               5

<210> SEQ ID NO 49
<211> LENGTH: 11
<212> TYPE: PRT
<213> ORGANISM: Homo sapiens

<400> SEQUENCE: 49

Ala Ala Trp Asp Asp Ser Leu Ser Gly Tyr Val
1               5                   10

<210> SEQ ID NO 50
<211> LENGTH: 324
<212> TYPE: DNA
<213> ORGANISM: Homo sapiens

<400> SEQUENCE: 50
caggctgtgc tcactcagcc gtcggggacc cccgggcaga gggtcaccct ctcttgttct    60
ggaagcagtt ccaacatcgg aagtaatact gtctactggt accggcagct cccaggaacg   120
gcccccagac tcctcatcta tagttataat cagcggccct caggggtccc tgaccgattc   180
tctggctcca agtctggcac ctcagcctcc ctggccatca gtgggctccg gtccgaggat   240
gaggctgatt attactgtgc agcatgggat gacagcctga gtggttatgt cttcggaact   300
gggaccaagg tcaccgtcct aggt                                          324

<210> SEQ ID NO 51
<211> LENGTH: 121
<212> TYPE: PRT
<213> ORGANISM: Homo sapiens

<400> SEQUENCE: 51

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Phe Leu Thr Ser His Asp Gly Ser Asn Thr Lys Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Asp Asp Thr Ala Val Tyr Tyr Cys
                85                  90                  95

Ala Asn Gly Phe Cys Gly Ser Asn Cys Tyr Tyr Phe His His Trp Gly
            100                 105                 110

Arg Gly Thr Thr Val Thr Val Ser Ser
        115                 120

<210> SEQ ID NO 52
<211> LENGTH: 6
<212> TYPE: PRT
<213> ORGANISM: Homo sapiens

<400> SEQUENCE: 52

Ser Asp Tyr Gly Met His
1               5

<210> SEQ ID NO 53
<211> LENGTH: 18
<212> TYPE: PRT
<213> ORGANISM: Homo sapiens

<400> SEQUENCE: 53

Phe Leu Thr Ser His Asp Gly Ser Asn Thr Lys Tyr Ala Asp Ser Val
1               5                   10                  15

Lys Gly

<210> SEQ ID NO 54
<211> LENGTH: 13
<212> TYPE: PRT
<213> ORGANISM: Homo sapiens

<400> SEQUENCE: 54

Asn Gly Phe Cys Gly Ser Asn Cys Tyr Tyr Phe His His
1               5                   10

<210> SEQ ID NO 55
<211> LENGTH: 363
<212> TYPE: DNA
<213> ORGANISM: Homo sapiens

<400> SEQUENCE: 55

```
gaggtgcagc tggtggagtc tgggggaggc gtggtccagc ctggggaggtc cctgagactc      60
tcctgtgcag cctctggatt caccttcagt gactatggca tgcactgggt ccgccaggct     120
ccaggcaagg ggctggagtg ggtgtttctt acatcacatg atggaagtaa tacaaaatat     180
gcagactccg tgaagggccg attcaccatc tccagagaca attccaagaa cacggtgtat     240
ctgcaaatga acagcctgag agctgacgac acggctgtct attactgtgc gaacgggttt     300
tgtggttcta actgctatta cttccatcac tggggccggg gaaccacggt caccgtctcc     360
tca                                                                   363
```

<210> SEQ ID NO 56
<211> LENGTH: 110
<212> TYPE: PRT
<213> ORGANISM: Homo sapiens

<400> SEQUENCE: 56

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

His Tyr Pro Tyr Trp Phe Gln Gln Lys Pro Gly Gln Ala Pro Arg Thr
        35                  40                  45

Leu Ile Tyr Asp Thr Ser Asn Lys His Ser Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Leu Leu Ser Tyr Ser Gly
                85                  90                  95

Val Arg Val Phe Gly Gly Gly Thr Lys Leu Thr Val Leu Gly
            100                 105                 110

<210> SEQ ID NO 57
<211> LENGTH: 14
<212> TYPE: PRT
<213> ORGANISM: Homo sapiens

<400> SEQUENCE: 57

Gly Ser Ser Thr Gly Ala Val Thr Ser Gly His Tyr Pro Tyr
1               5                   10

<210> SEQ ID NO 58
<211> LENGTH: 7
<212> TYPE: PRT
<213> ORGANISM: Homo sapiens

<400> SEQUENCE: 58

Asp Thr Ser Asn Lys His Ser
1               5

<210> SEQ ID NO 59
<211> LENGTH: 9
<212> TYPE: PRT
<213> ORGANISM: Homo sapiens

<400> SEQUENCE: 59

Leu Leu Ser Tyr Ser Gly Val Arg Val
1               5

<210> SEQ ID NO 60
<211> LENGTH: 330
<212> TYPE: DNA
<213> ORGANISM: Homo sapiens

<400> SEQUENCE: 60

```
cagactgtgg tgactcagga gccctcactg actgtgtccc caggagggac agtcactctc      60
acctgtggct ccagcactgg agctgtcacc agtggtcatt atccctactg gttccagcag     120
aagcctggcc aagcccccag gacactgatt tatgatacaa gcaacaaaca ctcctggaca     180
cctgcccggt tctcaggctc cctccttggg ggcaaagctg ccctgaccct ttcgggtgcg     240
cagcctgagg atgaggctga gtattactgc ttgctctcct atagtggtgt tcgagtgttc     300
ggcggaggga ccaagctgac cgtcctaggt                                      330
```

<210> SEQ ID NO 61
<211> LENGTH: 123
<212> TYPE: PRT
<213> ORGANISM: Homo sapiens

<400> SEQUENCE: 61

Gln Val Gln Leu Val Gln Ser Gly Gly Gly Leu Val Gln Pro Gly Gly
1               5                   10                  15

Ser Gln Arg Leu Ser Cys Ala Ala Ser Gly Phe Gly Phe Ser Asn Tyr
            20                  25                  30

Ala Val Ser Trp Val Arg Gln Ala Pro Gly Thr Gly Leu Glu Trp Val
        35                  40                  45

Ala Gly Val Asn Gly Gly Gly Gln Asn Thr Phe Tyr Ala Asp Ser Val
    50                  55                  60

Lys Gly Arg Phe Thr Ile Ser Arg Asp Asn Ser Lys Lys Thr Val Tyr
65                  70                  75                  80

Leu Gln Met Asn Ser Leu Arg Val Glu Asp Thr Ala Ile Tyr Tyr Cys
                85                  90                  95

Ala Lys Asp Gly Arg Phe Arg Asn Arg Arg Pro Asp Gly Phe Asp Thr
            100                 105                 110

Trp Gly Gln Gly Thr Leu Val Thr Val Ser Ser
        115                 120

<210> SEQ ID NO 62
<211> LENGTH: 5
<212> TYPE: PRT
<213> ORGANISM: Homo sapiens

<400> SEQUENCE: 62

Asn Tyr Ala Val Ser
1               5

<210> SEQ ID NO 63
<211> LENGTH: 17

<210> SEQ ID NO 63
<211> LENGTH: (not shown)
<212> TYPE: PRT
<213> ORGANISM: Homo sapiens

<400> SEQUENCE: 63

Gly Val Asn Gly Gly Gly Gln Asn Thr Phe Tyr Ala Asp Ser Val Lys
1               5                   10                  15
Gly

<210> SEQ ID NO 64
<211> LENGTH: 14
<212> TYPE: PRT
<213> ORGANISM: Homo sapiens

<400> SEQUENCE: 64

Asp Gly Arg Phe Arg Asn Arg Arg Pro Asp Gly Phe Asp Thr
1               5                   10

<210> SEQ ID NO 65
<211> LENGTH: 369
<212> TYPE: DNA
<213> ORGANISM: Homo sapiens

<400> SEQUENCE: 65
caggtgcagc tggtgcagtc tgggggaggc ctggtacagc ctggggggtc ccagagactc     60
tcctgtgcag cctctggatt tggcttcagt aactatgccg tgagctgggt ccgccaggcc    120
cccgggacgg gcctggagtg ggtcgcaggt gttaatggtg gtggccaaaa cacattttat    180
gcagactccg tgaagggccg gttcaccatc tccagagaca attccaagaa gacggtatat    240
ctgcaaatga atagcctgag agtcgaggac acggccatat attactgtgc gaaagacggt    300
cggtttagga ataggaggcc ggatggtttt gatacgtggg gccaaggaac cctggtcacc    360
gtctcctca                                                            369

<210> SEQ ID NO 66
<211> LENGTH: 109
<212> TYPE: PRT
<213> ORGANISM: Homo sapiens

<400> SEQUENCE: 66

Ser Ser Glu Leu Thr Gln Asp Pro Asn Val Ser Val Ala Leu Gly Gln
1               5                   10                  15

Thr Val Arg Ile Thr Cys Gln Gly Asp Thr Leu Arg Asn Asn Phe Pro
            20                  25                  30

Thr Trp Tyr Gln Gln Lys Pro Gly Gln Ala Pro Val Leu Val Phe Tyr
        35                  40                  45

Gly Lys Asp Asn Arg Pro Ser Gly Ile Pro Asp Arg Phe Ser Gly Ser
    50                  55                  60

Arg Ser Gly Thr Thr Ala Ser Leu Val Ile Thr Gly Ala Gln Ala Gln
65                  70                  75                  80

Asp Glu Ala Asp Tyr Tyr Cys Asn Ser Arg Asp Ser Gly His His
                85                  90                  95

Leu Val Phe Gly Gly Gly Thr Lys Leu Thr Val Leu Gly
            100                 105

<210> SEQ ID NO 67
<211> LENGTH: 11
<212> TYPE: PRT
<213> ORGANISM: Homo sapiens

<400> SEQUENCE: 67

Gln Gly Asp Thr Leu Arg Asn Asn Phe Pro Thr
1               5                   10

<210> SEQ ID NO 68
<211> LENGTH: 7
<212> TYPE: PRT
<213> ORGANISM: Homo sapiens

<400> SEQUENCE: 68

Gly Lys Asp Asn Arg Pro Ser
1               5

<210> SEQ ID NO 69
<211> LENGTH: 11
<212> TYPE: PRT
<213> ORGANISM: Homo sapiens

<400> SEQUENCE: 69

Asn Ser Arg Asp Ser Gly Gly His His Leu Val
1               5                   10

<210> SEQ ID NO 70
<211> LENGTH: 327
<212> TYPE: DNA
<213> ORGANISM: Homo sapiens

<400> SEQUENCE: 70
tcttctgagc tgactcagga ccctaatgtg tctgtggcct tgggacagac agtcaggatc      60
acatgccaag gtgacaccct cagaaataat tttccaacct ggtaccagca gaagccagga     120
caggcccctg tcctcgtctt ctatggtaaa gataatcggc cctcagggat cccagaccga     180
ttctctggct ccaggtcagg caccacagct tccttggtca tcactgggcc tcaggcgcaa     240
gatgaggccg actattactg taactcccgg gacagcgggg tcaccatctc ggttttcggc     300
ggagggacca gctgaccgt cctaggt                                          327

<210> SEQ ID NO 71
<211> LENGTH: 123
<212> TYPE: PRT
<213> ORGANISM: Homo sapiens

<400> SEQUENCE: 71

Gln Val Gln Leu Val Gln Ser Gly Gly Gly Val Val Gln Pro Gly Gly
1               5                   10                  15

Ser Leu Arg Leu Ser Cys Ala Ala Ser Gly Phe Thr Phe Ser Arg Tyr
                20                  25                  30

Ala Met Ser Trp Val Arg Gln Ala Pro Gly Lys Gly Leu Glu Trp Val
            35                  40                  45

Ser Ala Met Ser Gly Ser Gly Asp Thr Thr Tyr Tyr Ala Asp Ser Val
        50                  55                  60

Lys Gly Arg Phe Thr Ile Ser Arg Asp Asn Ser Lys Lys Thr Val Tyr
65                  70                  75                  80

Leu Gln Met Asn Arg Leu Arg Val Glu Asp Thr Ala Ile Tyr Tyr Cys
                85                  90                  95

Ala Lys Asp Gly Arg Phe Arg Asn Arg Arg Ser Asp Gly Phe Asp Thr
            100                 105                 110

Trp Gly Gln Gly Thr Leu Val Thr Val Ser Ser
        115                 120

<210> SEQ ID NO 72
<211> LENGTH: 5

<212> TYPE: PRT
<213> ORGANISM: Homo sapiens

<400> SEQUENCE: 72

Arg Tyr Ala Met Ser
1               5

<210> SEQ ID NO 73
<211> LENGTH: 17
<212> TYPE: PRT
<213> ORGANISM: Homo sapiens

<400> SEQUENCE: 73

Ala Met Ser Gly Ser Gly Asp Thr Thr Tyr Tyr Ala Asp Ser Val Lys
1               5                   10                  15

Gly

<210> SEQ ID NO 74
<211> LENGTH: 14
<212> TYPE: PRT
<213> ORGANISM: Homo sapiens

<400> SEQUENCE: 74

Asp Gly Arg Phe Arg Asn Arg Ser Asp Gly Phe Asp Thr
1               5                   10

<210> SEQ ID NO 75
<211> LENGTH: 369
<212> TYPE: DNA
<213> ORGANISM: Homo sapiens

<400> SEQUENCE: 75
caggtgcagc tggtgcagtc tggggggaggc gtggtacagc ctggggggtc cctgagactc      60
tcctgtgcag cctctggatt cacctttagc agatatgcca tgagttgggt ccgccaggct     120
ccagggaagg ggctggagtg gtctcagct atgagtggta gtggtgatac cacatactac     180
gcagactccg tgaagggccg gttcaccatc tccagagaca attccaagaa cacggtatat     240
ctgcaaatga atcgcctgag agtcgaggac acggccatat attactgtgc gaaagacggt     300
cggtttagga ataggaggtc ggatggtttt gatacgtggg gccaaggcac cctggtcacc     360
gtctcctca                                                             369

<210> SEQ ID NO 76
<211> LENGTH: 109
<212> TYPE: PRT
<213> ORGANISM: Homo sapiens

<400> SEQUENCE: 76

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asp Asn Arg Pro Ser Gly Ile Pro Arg Phe Ser Gly Ser
        50                  55                  60

Ser Ser Gly Asn Ala Ala Ser Leu Thr Ile Thr Gly Ala Gln Ala Glu
65                  70                  75                  80

Asp Glu Ala Asp Tyr Tyr Cys Asn Ser Arg Asp Thr Ser Gly Asn His
                85                  90                  95

Leu Val Phe Gly Gly Gly Thr Lys Val Thr Val Leu Gly
            100                 105

<210> SEQ ID NO 77
<211> LENGTH: 11
<212> TYPE: PRT
<213> ORGANISM: Homo sapiens

<400> SEQUENCE: 77

Gln Gly Asp Ser Leu Arg Ser Tyr Tyr Ala Ser
1               5                   10

<210> SEQ ID NO 78
<211> LENGTH: 7
<212> TYPE: PRT
<213> ORGANISM: Homo sapiens

<400> SEQUENCE: 78

Gly Lys Asp Asn Arg Pro Ser
1               5

<210> SEQ ID NO 79
<211> LENGTH: 11
<212> TYPE: PRT
<213> ORGANISM: Homo sapiens

<400> SEQUENCE: 79

Asn Ser Arg Asp Thr Ser Gly Asn His Leu Val
1               5                   10

<210> SEQ ID NO 80
<211> LENGTH: 327
<212> TYPE: DNA
<213> ORGANISM: Homo sapiens

<400> SEQUENCE: 80
tcttctgagc tgactcagga ccctgctgtg tctgtggcct tgggacagac agtcaggatc      60
acatgccaag agacagcct cagaagctat tatgcaagct ggtaccagca gaagccagga     120 caggccctg tacttgtcat ctatggtaaa gacaaccggc cctcagggat cccagaccga     180
ttctctggct ccagttcagg aaacgcagct tccttgacca tcactggggc tcaggcggaa     240
gatgaggctg actattactg taactcccgg gacaccagtg gtaaccatct ggtgttcggc     300
ggagggacca aggtcaccgt cctaggt                                         327

<210> SEQ ID NO 81
<211> LENGTH: 125
<212> TYPE: PRT
<213> ORGANISM: Homo sapiens

<400> SEQUENCE: 81

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys

Ala Arg Ala Lys Arg Phe Ala Ala Arg Arg Gly Leu Asp Ala Phe
            100                 105                 110

Asp Ile Trp Gly Gln Gly Thr Met Val Thr Val Ser Ser
        115                 120                 125

<210> SEQ ID NO 82
<211> LENGTH: 5
<212> TYPE: PRT
<213> ORGANISM: Homo sapiens

<400> SEQUENCE: 82

Ser Tyr Ala Ile Ser
1               5

<210> SEQ ID NO 83
<211> LENGTH: 17
<212> TYPE: PRT
<213> ORGANISM: Homo sapiens

<400> SEQUENCE: 83

Arg Ile Ile Pro Ile Leu Gly Ile Ala Asn Tyr Ala Gln Lys Phe Gln
1               5                   10                  15

Gly

<210> SEQ ID NO 84
<211> LENGTH: 16
<212> TYPE: PRT
<213> ORGANISM: Homo sapiens

<400> SEQUENCE: 84

Ala Lys Arg Phe Ala Ala Arg Arg Gly Leu Asp Ala Phe Asp Ile
1               5                   10                  15

<210> SEQ ID NO 85
<211> LENGTH: 375
<212> TYPE: DNA
<213> ORGANISM: Homo sapiens

<400> SEQUENCE: 85
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaagg atcatcccta ccttggtat agcaaactac     180 gcacagaagt tccagggcag agtcacgatt accgcggaca atccacgag cacagcctac     240 atggagctga gcagcctgag atctgaggac acggccgtgt attactgtgc gagagcaaag     300
cgctttgcag cagctcgtcg cgggctagat gcttttgata tctggggcca agggacaatg     360
gtcaccgtct cctca                                                      375

<210> SEQ ID NO 86
<211> LENGTH: 109
<212> TYPE: PRT
<213> ORGANISM: Homo sapiens

<400> SEQUENCE: 86

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr

```
              35                  40                  45
Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                 85                  90                  95

Leu Val Phe Gly Gly Gly Thr Lys Leu Thr Val Leu Gly
            100                 105

<210> SEQ ID NO 87
<211> LENGTH: 11
<212> TYPE: PRT
<213> ORGANISM: Homo sapiens

<400> SEQUENCE: 87

Gln Gly Asp Ser Leu Arg Ser Tyr Tyr Ala Ser
 1               5                  10

<210> SEQ ID NO 88
<211> LENGTH: 7
<212> TYPE: PRT
<213> ORGANISM: Homo sapiens

<400> SEQUENCE: 88

Gly Lys Asn Asn Arg Pro Ser
 1               5

<210> SEQ ID NO 89
<211> LENGTH: 11
<212> TYPE: PRT
<213> ORGANISM: Homo sapiens

<400> SEQUENCE: 89

Asn Ser Arg Asp Ser Ser Gly Asn His Leu Val
 1               5                  10

<210> SEQ ID NO 90
<211> LENGTH: 327
<212> TYPE: DNA
<213> ORGANISM: Homo sapiens

<400> SEQUENCE: 90
tcttctgagc tgactcagga ccctgctgtg tctgtggcct tgggacagac agtccggatc      60
acatgccaag agacagcct cagaagctat tatgcaagct ggtaccagca gaagccagga     120
caggcccctg tacttgtcat ctatggtaaa aacaaccggc cctcagggat cccagaccga     180
ttctctggct ccagctcagg aaacacagct tccttgacca tcactggggc tcaggcggaa     240
gatgaggctg actattactg taactcccgg gacagcagtg gtaaccatct ggtattcggc     300
ggagggacca agctgaccgt cctaggt                                         327

<210> SEQ ID NO 91
<211> LENGTH: 117
<212> TYPE: PRT
<213> ORGANISM: Homo sapiens

<400> SEQUENCE: 91

Gln Val Thr Leu Lys Glu Ser Gly Gly Asp Leu Val Lys Pro Gly Gly
 1               5                  10                  15

Ser Leu Arg Leu Ser Cys Ala Ala Ser Gly Phe Thr Phe Arg Lys Tyr
             20                  25                  30
```

```
Tyr Met Ala Trp Ile Arg Gln Ala Pro Gly Lys Gly Pro Glu Trp Leu
         35                  40                  45
Ser Thr Ile Ser Asn Ser Gly Asp Ile Ile Asp Tyr Ala Asp Ser Val
 50                  55                  60
Arg Gly Arg Phe Ser Ile Ser Arg Asp Asn Ala Gln Lys Ser Leu Tyr
 65                  70                  75                  80
Leu Gln Met Thr Ser Leu Arg Pro Asp Asp Ser Ala Ile Tyr Tyr Cys
             85                  90                  95
Ala Arg Glu Tyr Phe Phe Ser Phe Asp Val Trp Gly Arg Gly Thr Leu
            100                 105                 110
Val Thr Val Ser Ser
            115

<210> SEQ ID NO 92
<211> LENGTH: 5
<212> TYPE: PRT
<213> ORGANISM: Homo sapiens

<400> SEQUENCE: 92

Lys Tyr Tyr Met Ala
 1               5

<210> SEQ ID NO 93
<211> LENGTH: 17
<212> TYPE: PRT
<213> ORGANISM: Homo sapiens

<400> SEQUENCE: 93

Thr Ile Ser Asn Ser Gly Asp Ile Ile Asp Tyr Ala Asp Ser Val Arg
 1               5                  10                  15
Gly

<210> SEQ ID NO 94
<211> LENGTH: 8
<212> TYPE: PRT
<213> ORGANISM: Homo sapiens

<400> SEQUENCE: 94

Glu Tyr Phe Phe Ser Phe Asp Val
 1               5

<210> SEQ ID NO 95
<211> LENGTH: 351
<212> TYPE: DNA
<213> ORGANISM: Homo sapiens

<400> SEQUENCE: 95
caggttacct tgaaggagtc tgggggagac ttggtcaagc ccggagggtc cctaagactc      60
tcatgtgcag cctctggatt caccttcaga aagtattaca tggcctggat ccgccaggct     120
ccagggaagg ggccggagtg gctttcaacc attagtaaca gcggtgatat catagactat     180
gcagactctg tgaggggccg gttctccatc tccaggaca atgcccagaa gtcactgtat      240
ctgcaaatga cctccctgag acccgacgac tcggccatct attactgtgc gagggaatat     300
ttcttttctt ttgatgtgtg gggccgaggc accctggtca ccgtctcctc a              351

<210> SEQ ID NO 96
<211> LENGTH: 109
<212> TYPE: PRT
<213> ORGANISM: Homo sapiens
```

-continued

<400> SEQUENCE: 96

Ser Ser Glu Leu Thr Gln Asp Pro Ala Val Ser Val Ala Leu Gly Gln
1               5                   10                  15

Thr Ile Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Lys Arg Pro Ser Gly Ile Pro Asp Arg Ile Ser Gly Ser
    50                  55                  60

Arg Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Leu Val Phe Gly Gly Gly Thr Gln Leu Thr Val Leu Gly
            100                 105

<210> SEQ ID NO 97
<211> LENGTH: 11
<212> TYPE: PRT
<213> ORGANISM: Homo sapiens

<400> SEQUENCE: 97

Gln Gly Asp Ser Leu Arg Ser Tyr Tyr Ala Ser
1               5                   10

<210> SEQ ID NO 98
<211> LENGTH: 7
<212> TYPE: PRT
<213> ORGANISM: Homo sapiens

<400> SEQUENCE: 98

Gly Lys Asn Lys Arg Pro Ser
1               5

<210> SEQ ID NO 99
<211> LENGTH: 11
<212> TYPE: PRT
<213> ORGANISM: Homo sapiens

<400> SEQUENCE: 99

Asn Ser Arg Asp Ser Ser Gly Asn His Leu Val
1               5                   10

<210> SEQ ID NO 100
<211> LENGTH: 327
<212> TYPE: DNA
<213> ORGANISM: Homo sapiens

<400> SEQUENCE: 100
tcttctgagc tgactcagga ccctgctgtg tctgtggccc tgggacagac aatcaggatc      60
acatgccaag agacagcct cagaagctat tatgcaagct ggtaccagca aaagccagga     120
caggcccctg tacttgtcat ctatggtaaa aacaagcggc cctcagggat cccagaccga     180
atctctggct ccaggtcagg aaacacagct tccttgacca tcactggggc tcaggcggaa     240
gatgaggctg actattactg taactcccgg gacagcagtg gaaaccatct ggtgttcggc     300
ggagggaccc agctcaccgt tttaggt                                         327

<210> SEQ ID NO 101
<211> LENGTH: 114
<212> TYPE: PRT

<213> ORGANISM: Homo sapiens

<400> SEQUENCE: 101

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Ile His Asn
            20                  25                  30

Ser Asn Val Lys Asn Cys Leu Ala Trp Tyr Gln Gln Lys Leu Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ser Ile Gln Leu Pro Arg Thr Phe Gly Gln Gly Thr Lys Val Glu Ile
            100                 105                 110

Lys Arg

<210> SEQ ID NO 102
<211> LENGTH: 17
<212> TYPE: PRT
<213> ORGANISM: Homo sapiens

<400> SEQUENCE: 102

Lys Ser Ser Gln Ser Val Ile His Asn Ser Asn Val Lys Asn Cys Leu
1               5                   10                  15

Ala

<210> SEQ ID NO 103
<211> LENGTH: 7
<212> TYPE: PRT
<213> ORGANISM: Homo sapiens

<400> SEQUENCE: 103

Trp Ala Ser Thr Arg Glu Ser
1               5

<210> SEQ ID NO 104
<211> LENGTH: 9
<212> TYPE: PRT
<213> ORGANISM: Homo sapiens

<400> SEQUENCE: 104

Met Gln Ser Ile Gln Leu Pro Arg Thr
1               5

<210> SEQ ID NO 105
<211> LENGTH: 342
<212> TYPE: DNA
<213> ORGANISM: Homo sapiens

<400> SEQUENCE: 105
gacatcgtga tgacccagtc tccagactcc ctggctgtgt ctctgggcga gagggccacc      60
atcaactgca agtccagcca gagtgttata cacaactcca acgttaagaa ttgcttagct     120
tggtaccagc agaaattagg acagcctcct aacctgctca tttactgggc ctctacccgg     180
gagtccgggg tccctgaccg attcagtggc agcgggtcag ggacagattt cacactgaaa     240
atcagccggg tggaggctga ggatgttggg gtttattact gtatgcaaag tatacagctt     300

```
ccgaggacgt tcggccaagg gaccaaggtg gaaatcaaac gt                    342
```

<210> SEQ ID NO 106
<211> LENGTH: 14
<212> TYPE: PRT
<213> ORGANISM: HIV

<400> SEQUENCE: 106

Met Gly Tyr Gly Arg Lys Lys Arg Arg Gln Arg Arg Arg Gly
1               5                   10

HUMAN ANTI-AMYLOID BETA PEPTIDE ANTIBODY AND FRAGMENT OF SAID ANTIBODY

TECHNICAL FIELD

The present invention relates to a human anti-amyloid β peptide (hereinafter referred to as "Aβ") antibody that binds to Aβ to thereby inhibit aggregation of Aβ molecules, and a fragment of said antibody. The antibody and a fragment thereof according to the present invention are expected to be useful as a medicament for the diagnosis and treatment of Alzheimer dementia wherein aggregates formation of Aβ molecules and its toxicity are thought to be one of etiologies of this disease.

BACKGROUND ART

Although an onset mechanism of Alzheimer dementia has not yet been fully elucidated, it is thought that toxicity to neuronal cells of aggregates of Aβ molecules may play an important role. A matter of aggregates formation of Aβ molecules is a matter of conformation of Aβ molecules.

Aβ molecules are degradation products produced by cleavage of neuronal amyloid precursor proteins with e.g. β secretase and include two variants, i.e. Aβ1-40 and Aβ1-42 (hereinafter referred to as "Aβ42"). Among the two variants, it is reported that Aβ42 is more likely to aggregate and is more correlated with diseases and neurotoxicity than Aβ1-40. Also, localization of microglias and astrocytes in Aβ plaques present in the brain is observed and is suggested to correlate with neurotoxicity.

It is hypothesized that accumulation of Aβ, when viewed from different angle, may be an aging process of individuals and hence, when accumulation of Aβ exceeds its threshold value as a consequence of loss of balance in clearance, onset of disease results. Based on these hypotheses, there have been attempts to develop a small molecular size inhibitor to β secretase involved in cleavage of the precursor protein so as to inhibit the Aβ production per se. However, a mechanism of Aβ production is not so plain and the results obtained heretofore are not necessarily satisfactory.

On the other hand, a report by B. Solomon et al. (see Non-patent reference 1) for in vitro inhibition of Aβ aggregation with an anti-Aβ antibody, an antibody to the N-terminal of Aβ, and a report by Schenk et al. (see Non-patent reference 2) that administration of Aβ42 prior to aggregation in admixture with adjuvant to mice reduced deposition of cerebral amyloids, had opened up a road to a new immunotherapy. In fact, a vaccine therapy for Alzheimer dementia with Aβ has been attempted to prove its efficacy to some extent, such as reduction in deposition of cerebral amyloids (see Non-patent references 3 and 4). However, while efficacy may be observed with a vaccine therapy, serious detrimental side effects may also be seen due to induction of inflammatory reactions by activation of T cells and thus a vaccine therapy has not yet been established as a safe and efficacious approach for the prophylaxis and treatment of the disease.

It is presumed that efficacy of an Aβ vaccine therapy may be due to localized, activated microglia cells that take in via Fc receptor and decompose deposited Aβ antigen-antibody complex and that may bind to a soluble Aβ to prevent local deposition.

On the other hand, McLaurin et al. demonstrated that passive immunity with an antibody to Aβ4-10, a terminal portion of Aβ molecule, could effectively inhibit or delay onset of disease in experiments performed in mice (see Non-patent reference 5). In case of passive immunity for transfer of an antibody, induction of an inflammatory reaction due to activation of T cells is unlikely to occur but as little as 0.1% or less of anti-Aβ antibodies in serum may pass through the blood-brain barrier to thereby necessitate frequent administration of a large amount.

Non-patent reference 1: Solomon, B. et al., (1996) Pro. Natl. Acad. Sci., 93, 452-455

Non-patent reference 2: Schenk, D. et al., (1999) Nature, 400, 173

Non-patent reference 3: Nicoll, J. A. et al., (2003) Nature Medicine, 9, 448

Non-patent reference 4: Monsonego, A. et al., (2003) Science, 302, 834-838

Non-patent reference 5: McLaurin et al., (2002) Nature Medicine, 8, 1263-1269

DISCLOSURE OF THE INVENTION

Technical Problem to be Solved by the Invention

For addressing a risk of detrimental side effects as well as frequent administration of a large amount, lowered immunogenicity of an antibody per se is significant. Besides, it is also reported that an antibody in a smaller size would be advantageous for transfer through the blood-brain barrier. It is thus expected that a wholly human antibody that is specific to Aβ molecule and that may be made in a smaller size would be highly efficacious as a medicament for treating Alzheimer dementia.

Moreover, a matter of aggregates formation of Aβ molecules is a matter of conformation of Aβ molecules. Therefore, the presence of a molecule that may inhibit or regulate a structural change of Aβ molecules, i.e. a chaperone-like molecule specific to Aβ molecules, would provide possibility to regulate aggregates formation of Aβ molecules. An antibody with a chaperone-like activity has been reported and hence an anti-Aβ antibody may also be well expected to have such activity.

In addition, for diagnosis of Alzheimer dementia, amyloid imaging approach for early detection of formation and deposition of abnormal Aβ molecules has drawn attention wherein development of probe techniques is essential. However, an intracerebral imaging technique has not yet been developed that may specifically detect abnormal Aβ molecules with high sensitivity. Thus, capacity to pass through the blood-brain barrier and to detect early intracerebral deposition of abnormal Aβ molecules would lead to excellent diagnosis of the disease.

Means for Solving the Problems

With the views mentioned above, the present inventors isolated human antibodies that may specifically bind to Aβ42 with a human antibody phage display library to thereby succeed in isolation of six human single chain variable regions (scFv), which may specifically bind to Aβ42, and of a VL chain which could exert binding specificity to Aβ with a light (L) chain variable region (VL chain or VL) alone of an antibody unlike ordinary scFv. Moreover, the present inventors have found that these scFvs and VL chain inhibited aggregation of Aβ to thereby have completed the present invention.

Thus, the present invention encompasses the inventions (1) to (32) as described below for methods and materials that may be useful from medical and industrial point of view.

(1) A human anti-amyloid β peptide (Aβ) antibody that may bind to Aβ.

(2) The human anti-Aβ antibody according to (1) wherein complementarity determining region (CDR) of H chain has the amino acid sequence depicted either in (a) or (b) below and complementarity determining region (CDR) of L chain has the amino acid sequence depicted either in (c) or (d) below:

(a) the amino acid sequences as depicted in any one of SEQ ID NO: 2, 12, 22, 32, 42, 52, 62, 72, 82 or 92 for CDR1, in any one of SEQ ID NO: 3, 13, 23, 33, 43, 53, 63, 73, 83 or 93 for CDR2, and in any one of SEQ ID NO: 4, 14, 24, 34, 44, 54, 64, 74, 84 or 94 for CDR3;

(b) the amino acid sequences as depicted in SEQ ID NOs: 2-4, 12-14, 22-24, 32-34, 42-44, 52-54, 62-64, 72-74, 82-84 or 92-94, or said amino acid sequences with substitution, deletion, insertion and/or addition of one or more amino acid residues that may serve as complementarity determining region of H chain to Aβ, for CDRs 1-3;

(c) the amino acid sequences as depicted in any one of SEQ ID NO: 7, 17, 27, 37, 47, 57, 67, 77, 87, 97 or 102 for CDR1, in any one of SEQ ID NO: 8, 18, 28, 38, 48, 58, 68, 78, 88, 98 or 103 for CDR2, and in any one of SEQ ID NO: 9, 19, 29, 39, 49, 59, 69, 79, 89, 99 or 104 for CDR3;

(d) the amino acid sequences as depicted in SEQ ID NOs: 7-9, 17-19, 27-29, 37-39, 47-49, 57-59, 67-69, 77-79, 87-89, 97-99 or 102-104, or said amino acid sequences with substitution, deletion, insertion and/or addition of one or more amino acid residues that may serve as complementarity determining region of L chain to Aβ, for CDRs 1-3.

(3) The human anti-Aβ antibody according to (2) wherein the amino acid sequences of CDRs 1-3 for H chain are those selected from combinations of SEQ ID NOs: 2-4, 12-14, 22-24, 32-34, 42-44, 52-54, 62-64, 72-74, 82-84 or 92-94, and the amino acid sequences of CDRs 1-3 for L chain are those selected from combinations of SEQ ID NOs: 7-9, 17-19, 27-29, 37-39, 47-49, 57-59, 67-69, 77-79, 87-89, 97-99 or 102-104.

(4) The human anti-Aβ antibody according to (3) wherein the amino acid sequences of a combination of CDRs 1-3 for H chain and CDRs 1-3 for L chain are any of combinations of SEQ ID NOs: 2-4 and 7-9, SEQ ID NOs: 12-14 and 17-19, SEQ ID NOs: 22-24 and 27-29, SEQ ID NOs: 32-34 and 37-39, SEQ ID NOs: 42-44 and 47-49, SEQ ID NOs: 52-54 and 57-59, SEQ ID NOs: 62-64 and 67-69, SEQ ID NOs: 72-74 and 77-79, SEQ ID NOs: 82-84 and 87-89 or SEQ ID NOs: 92-94 and 97-99.

(5) The human anti-Aβ antibody according to any one of (1) to (4) wherein H chain variable region has the amino acid sequence depicted either in (e) or (f) below and L chain variable region has the amino acid sequence depicted either in (g) or (h) below:

(e) the amino acid sequence selected from any one of SEQ ID NO: 1, 11, 21, 31, 41, 51, 61, 71, 81 or 91;

(f) the amino acid sequence as depicted in any one of SEQ ID NO: 1, 11, 21, 31, 41, 51, 61, 71, 81 or 91 with substitution, deletion, insertion and/or addition of one or more amino acid residues that may serve as H chain variable region to Aβ;

(g) the amino acid sequence selected from any one of SEQ ID NO: 6, 16, 26, 36, 46, 56, 66, 77, 86, 96 or 101;

(h) the amino acid sequence as depicted in any one of SEQ ID NO: 6, 16, 26, 36, 46, 56, 66, 77, 86, 96 or 101 with substitution, deletion, insertion and/or addition of one or more amino acid residues that may serve as L chain variable region to Aβ.

(6) The human anti-Aβ antibody according to any one of (1) to (5) wherein the amino acid sequences of a combination of H chain variable region and L chain variable region are those of a combination of SEQ ID NOs: 1 and 6, SEQ ID NOs: 11 and 16, SEQ ID NOs: 21 and 26, SEQ ID NOs: 31 and 36, SEQ ID NOs: 41 and 46, SEQ ID NOs: 51 and 56, SEQ ID NOs: 61 and 66, SEQ ID NOs: 71 and 76, SEQ ID NOs: 81 and 86, or SEQ ID NOs: 91 and 96.

(7) The human anti-Aβ antibody according to any one of (1) to (6) wherein said Aβ is fibrillar Aβ.

(8) An H chain variable region fragment of a human anti-amyloid β peptide (Aβ) antibody that may bind to Aβ.

(9) The H chain variable region fragment of a human anti-Aβ antibody according to (8) wherein complementarity determining region (CDR) has the amino acid sequence depicted either in (a) or (b) below:

(a) the amino acid sequences as depicted in any one of SEQ ID NO: 2, 12, 22, 32, 42, 52, 62, 72, 82 or 92 for CDR1, in any one of SEQ ID NO: 3, 13, 23, 33, 43, 53, 63, 73, 83 or 93 for CDR2, and in any one of SEQ ID NO: 4, 14, 24, 34, 44, 54, 64, 74, 84 or 94 for CDR3;

(b) the amino acid sequences as depicted in SEQ ID NOs: 2-4, 12-14, 22-24, 32-34, 42-44, 52-54, 62-64, 72-74, 82-84 or 92-94, or said amino acid sequences with substitution, deletion, insertion and/or addition of one or more amino acid residues that may serve as complementarity determining region of H chain to Aβ, for CDRs 1-3.

(10) The H chain variable region fragment of a human anti-Aβ antibody according to (9) wherein the amino acid sequences of CDRs 1-3 are those selected from combinations of SEQ ID NOs: 2-4, 12-14, 22-24, 32-34, 42-44, 52-54, 62-64, 72-74, 82-84 or 92-94.

(11) The H chain variable region fragment of a human anti-Aβ antibody according to any one of (8) to (10) wherein said fragment has the amino acid sequence depicted either in (e) or (f) below:

(e) the amino acid sequence selected from any one of SEQ ID NO: 1, 11, 21, 31, 41, 51, 61, 71, 81 or 91;

(f) the amino acid sequence as depicted in any one of SEQ ID NO: 1, 11, 21, 31, 41, 51, 61, 71, 81 or 91 with substitution, deletion, insertion and/or addition of one or more amino acid residues that may serve as H chain variable region to Aβ.

(12) The H chain variable region fragment of a human anti-Aβ antibody according to any one of (8) to (11) wherein said Aβ is fibrillar Aβ.

(13) An L chain variable region fragment of a human anti-amyloid β peptide (Aβ) antibody that may bind to Aβ.

(14) The L chain variable region fragment of a human anti-Aβ antibody according to (13) wherein complementarity determining region (CDR) has the amino acid sequence depicted either in (c) or (d) below:

(c) the amino acid sequences as depicted in any one of SEQ ID NO: 7, 17, 27, 37, 47, 57, 67, 77, 87, 97 or 102 for CDR1, in any one of SEQ ID NO: 8, 18, 28, 38, 48, 58, 68, 78, 88, 98 or 103 for CDR2, and in any one of SEQ ID NO: 9, 19, 29, 39, 49, 59, 69, 79, 89, 99 or 104 for CDR3;

(d) the amino acid sequences as depicted in SEQ ID NOs: 7-9, 17-19, 27-29, 37-39, 47-49, 57-59, 67-69, 77-79, 87-89, 97-99 or 102-104, or said amino acid sequences with substitution, deletion, insertion and/or addition of one or more amino acid residues that may serve as complementarity determining region of L chain to Aβ, for CDRs 1-3.

(15) The L chain variable region fragment of a human anti-Aβ antibody according to (14) wherein the amino acid sequences of CDRs 1-3 are those selected from combinations of SEQ ID NOs: 7-9, 17-19, 27-29, 37-39, 47-49, 57-59, 67-69, 77-79, 87-89, 97-99 or 102-104.

(16) The L chain variable region fragment of a human anti-Aβ antibody according to any one of (8) to (10) wherein said fragment has the amino acid sequence depicted either in (g) or (h) below:

(g) the amino acid sequence selected from any one of SEQ ID NO: 6, 16, 26, 36, 46, 56, 66, 77, 86, 96 or 101;

(h) the amino acid sequence as depicted in any one of SEQ ID NO: 6, 16, 26, 36, 46, 56, 66, 77, 86, 96 or 101 with substitution, deletion, insertion and/or addition of one or more amino acid residues that may serve as L chain variable region to Aβ.

(17) The L chain variable region fragment of a human anti-Aβ antibody according to any one of (13) to (16) wherein said Aβ is fibrillar Aβ.

(18) A single chain variable region fragment of a human-derived antibody to Aβ comprising the H chain variable region fragment of a human anti-Aβ antibody according to any one of (8) to (12) and the L chain variable region fragment of a human anti-Aβ antibody according to any one of (13) to (17) bound to each other.

(19) A human-derived antibody to Aβ or a fragment of said antibody comprising a constant region of a human-derived antibody bound to the H chain variable region fragment of a human anti-Aβ antibody according to any one of (8) to (12) and/or to the L chain variable region fragment of a human anti-Aβ antibody according to any one of (13) to (17).

(20) The antibody fragment according to (19) wherein said antibody fragment is Fab, Fab', F(ab')$_2$, scAb, or scFv-Fc.

(21) A human-derived antibody to Aβ or a fragment of said antibody comprising an L chain variable region fragment of a human anti-Aβ antibody having the amino acid sequence as depicted in SEQ ID NO: 101 and a constant region of a human-derived antibody bound to each other.

(22) A fused antibody or a fragment thereof comprising the antibody or a fragment thereof according to any one of (1) to (21) fused to a peptide or other protein.

(23) A modified antibody or a fragment thereof comprising the antibody or the fused antibody or a fragment thereof according to any one of (1) to (22) bound to a modifying agent.

(24) A gene coding for the antibody or the fused antibody or a fragment thereof according to any one of (1) to (22).

(25) A recombinant expression vector comprising the gene according to (24).

(26) A transfectant with the gene according to (24) introduced therein.

(27) A method for producing a human anti-Aβ antibody or a fragment thereof by expression of the gene according to (24) in a host cell.

(28) A genetic medicament comprising the gene according to (24).

(29) A reagent for detection of Aβ employing the antibody or a fragment thereof according to any one of (1) to (21), or the fused antibody or a fragment thereof according to (22), or the modified antibody or a fragment thereof according to (23).

(30) A diagnostic for Alzheimer dementia employing the antibody or a fragment thereof according to any one of (1) to (21), or the fused antibody or a fragment thereof according to (22), or the modified antibody or a fragment thereof according to (23).

(31) An inhibitor to A13 aggregation employing the antibody or a fragment thereof according to any one of (1) to (21), or the fused antibody or a fragment thereof according to (22), or the modified antibody or a fragment thereof according to (23).

(32) A medicament for the prophylaxis and treatment of Alzheimer dementia employing the antibody or a fragment thereof according to any one of (1) to (21), or the fused antibody or a fragment thereof according to (22), or the modified antibody or a fragment thereof according to (23).

These anti-Aβ antibodies and a fragment thereof, in spite of their small molecular size such as scFv or VL, were proved to effectively inhibit aggregation of Aβ in vitro. The antibody according to the present invention may be designed to pass through the blood-brain barrier via antibody engineering as it has a quite small molecular weight, including e.g. a fused antibody with transferrin to enable its transfer through the blood-brain barrier via a transferrin receptor and a bispecific antibody.

It is also possible to fuse the antibody with an antibody to P glycoprotein or with a protein or a small molecule that may interact with a receptor involved in drug transfer through the blood-brain barrier. Alternatively, it is also possible to display these antibodies on fibrous phages with excellent membrane permeability and low antigenicity for transfer into the brain, as reported by McCafferty et al., Nature, 348:552-554, 1990.

Alternatively, it is also possible to attach to these antibodies a region that may interact with Fc receptor so as to remove accumulated Aβ aggregates in the brain via their interaction with microglias.

The antibody according to the present invention, being a wholly human antibody, allows for not only diagnostic imaging but also development of a method for the treatment by inhibiting an aggregation process of Aβ molecules. Thus, the present invention would greatly contribute to therapy of Alzheimer dementia.

More Efficacious Effects than Prior Art

The human monoclonal antibody and a fragment thereof according to the present invention, comprising a variable region of a human-derived anti-Aβ antibody, strongly reacts with Aβ to thereby inhibit its aggregation and hence may be used as a medicament for the prophylaxis and treatment of Alzheimer dementia.

BEST MODE FOR CARRYING OUT THE INVENTION

Figure 1:
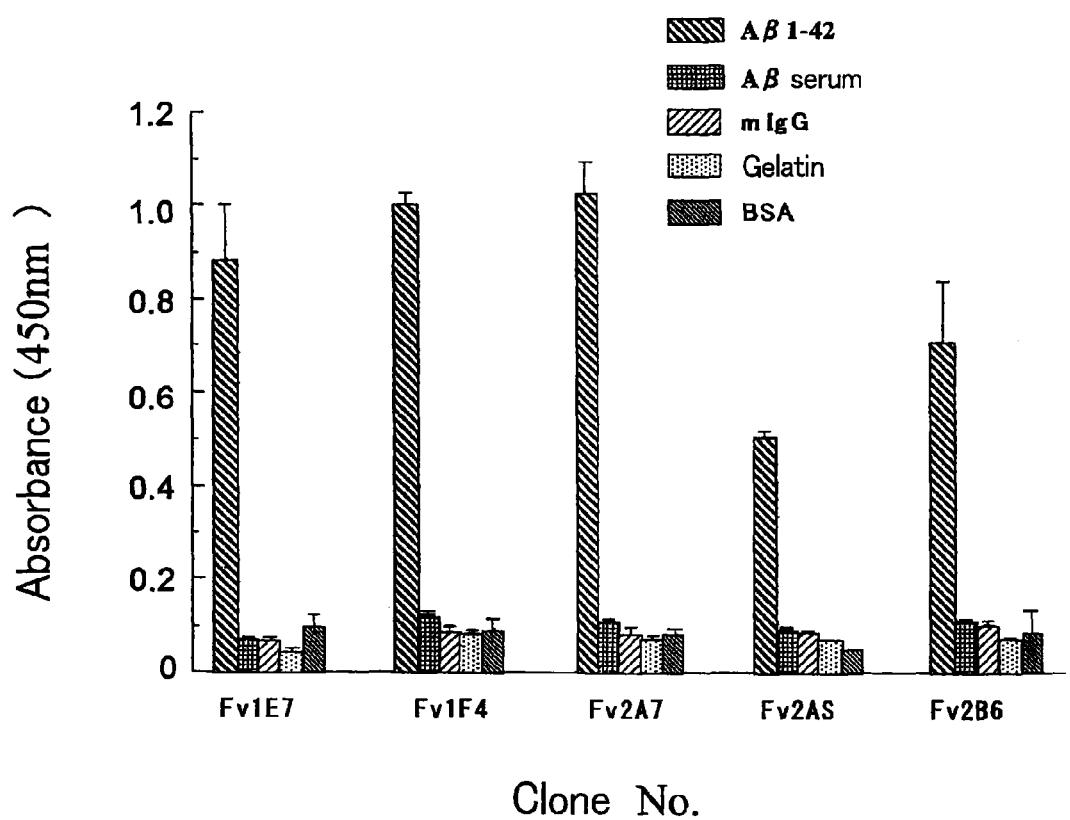
FIG. 1 is a graph showing the results of ELISA where specificity to Aβ42 peptide of scFv from the isolated clones was estimated.

The antibody and a fragment thereof such as scFv according to the present invention were obtained as described below.

From peripheral B lymphocytes taken from 20 healthy donors, cDNAs of each of immunoglobulin heavy (H) chain and light (L) chain were amplified by RT-PCR and combined together with a linker DNA to prepare scFv DNAs where the H chain variable region (VH chain or VH) and VL chain DNAs from lymphocytes of healthy donors were in random combination.

The scFv DNAs were incorporated into phagemid vector pCANTAB5E to prepare a scFv display phage library consisting of $10^9$ clones from healthy donors. This library was then combined with Aβ immobilized on a solid phase and an anti-Aβ scFv display phage clone was recovered, concentrated and screened. As a result, respective screened clones produced scFv antibody or VL fragment that bound to Aβ.

For expression of scFv or VL fragment, they may be expressed e.g. in *E. coli*. When expressed in *E. coli*, scFv may be expressed as being functionally bound with a conventional useful promoter, a signal sequence for secretion of an antibody, and the like. The promoter includes, for instance, lacZ promoter, araB promoter, and the like. For a signal sequence for secretion of scFv, pelB signal sequence (Lei, S P. et al., J. Bacteriol., 1987, 169: 4379-4383) may favorably be used. For secretion in culture supernatant, a signal sequence of g3 protein from M13 phage may be used.

Likewise, in case of VL fragment, it may be expressed alone or in the form of a fused protein as being bound with other peptides or proteins.

The thus expressed scFv may be isolated from within and without the host cells and purified to homogeneity. The scFv expressed in accordance with the present invention, as being bound with E tag sequence at its C-terminal, may easily be purified by affinity chromatography with an anti-E tag antibody in a short time. It may also be purified by a combination of the conventional methods commonly used for isolation and purification of a protein. For instance, ultrafiltration, salting-out, and different chromatography such as gel filtration/ion exchange/hydrophobic chromatography may be combined to isolate and purify the antibody.

The scFv protein and VL chain obtained in accordance with the present invention were found to bind to Aβ. Measurement for the antigen-binding activity of the anti-Aβ antibody as used herein includes ELISA, BIAcore, and the like. For ELISA, a sample containing the anti-Aβ antibody or a fragment thereof of interest, e.g. culture supernatant of *E. coli* or the purified antibody, may be added to a 96-well plate with immobilized Aβ. Then, a secondary antibody labeled with an enzyme such as peroxidase may be added to the plate. After incubation and washing of the plate, a developing substrate TMBZ may be added to the plate to measure absorbance for the estimation of the antigen-binding activity.

The thus obtained scFv and VL fragment were estimated for their ability to inhibit Aβ aggregation. As a consequence, it was revealed that the scFv and VL fragment could fully inhibit formation of Aβ aggregates.

This effect may be derived from binding to a normal type Aβ of the anti-Aβ antibody fragment of the present invention to thereby inhibit its structural conversion into an aggregate type Aβ. Such an effect implies that the antibody and a fragment thereof could well inhibit structural conversion into an aggregate type Aβ within the living body. Thus, these small sized antibodies may be expected for prophylactics for inhibiting the structural conversion of Aβ and also for a medicament for inhibiting progress of symptoms.

Besides, it was found that the anti-Aβ antibody fragment of the present invention comprises a sequence that reacts more strongly with an aggregate type Aβ than a normal type Aβ. It is thought that most of amyloids deposited in the brain are of an aggregate type Aβ or its fibrillar form, and reduction in cerebral amyloid deposition in the patients' brains observed in an attempt of pilot vaccine therapy is presumed to be due to the action of localized, activated microglia cells that take in via Fc receptor and decompose deposited Aβ antigen-antibody complex. Accordingly, the anti-Aβ antibody fragments of the present invention (Fv1E1, Fv1E4, Fv1E7, Fv2A7, Fv2A8, Fv2B6, B7, B6, F10, D1, and VLA2) may be divided into either:

(1) one which binds to a normal type Aβ alone to thereby inhibit its structural conversion into an aggregate type Aβ (VLA2);

(2) one which binds to an aggregate type Aβ or its fibrillar form alone to thereby remove an aggregate type Aβ, to inhibit increase in a fibrillar form of Aβ and to inhibit structural conversion of a normal type Aβ into an aggregate type Aβ (B6, F10, D1); or (3) one which possesses both properties (1) and (2) (Fv1E1, Fv1E4, Fv1E7, Fv2A7, Fv2A8, Fv2B6, B7).

Any of (1) to (3) may be a promising medicament for the treatment of Alzheimer diseases.

Amino acid sequences and nucleotide sequences encoding the same of each VH chain and VL chain of the ten scFv (Fv1E1, Fv1E4, Fv1E7, Fv2A7, Fv2A8, Fv2B6, B7, B6, F10, D1) and the VL chain (VLA2) as mentioned above having the inhibitory activity are described below.

(1) Fv1E1 Clone

The amino acid sequence of VH chain of the clone Fv1E1 is shown in SEQ ID NO: 1. Also, the amino acid sequences of CDR1 to CDR3 of said VH chain are shown in SEQ ID NOs: 2 to 4, respectively. Thus, in the amino acid sequence of VH chain as depicted in SEQ ID NO: 1, the amino acid sequence of the amino acid residues No. 30 to No. 35 corresponds to CDR1 (SEQ ID NO: 2), the amino acid sequence of the amino acid residues No. 50 to No. 66 to CDR2 (SEQ ID NO: 3), and the amino acid sequence of the amino acid residues No. 99 to No. 107 to CDR3 (SEQ ID NO: 4). The nucleotide sequence coding for the amino acid sequence of said VH chain is shown in SEQ ID NO: 5.

The amino acid sequence of VL chain of the clone Fv1E1 is shown in SEQ ID NO: 6. Also, the amino acid sequences of CDR1 to CDR3 of said VL chain are shown in SEQ ID NOs: 7 to 9, respectively. Thus, in the amino acid sequence of VL chain as depicted in SEQ ID NO: 6, the amino acid sequence of the amino acid residues No. 23 to No. 35 corresponds to CDR1 (SEQ ID NO: 7), the amino acid sequence of the amino acid residues No. 51 to No. 57 to CDR2 (SEQ ID NO: 8), and the amino acid sequence of the amino acid residues No. 90 to No. 100 to CDR3 (SEQ ID NO: 9). The nucleotide sequence coding for the amino acid sequence of said VL chain is shown in SEQ ID NO: 10.

(2) Fv1E4 Clone

The amino acid sequence of VH chain of the clone Fv1E4 is shown in SEQ ID NO: 11. Also, the amino acid sequences of CDR1 to CDR3 of said VH chain are shown in SEQ ID NOs: 12 to 14, respectively. Thus, in the amino acid sequence of VH chain as depicted in SEQ ID NO: 11, the amino acid sequence of the amino acid residues No. 30 to No. corresponds to CDR1 (SEQ ID NO: 12), the amino acid sequence of the amino acid residues No. 50 to No. 66 to CDR2 (SEQ ID NO: 13), and the amino acid sequence of the amino acid residues No. 99 to No. 112 to CDR3 (SEQ ID NO: 14). The nucleotide sequence coding for the amino acid sequence of said VH chain is shown in SEQ ID NO: 15.

The amino acid sequence of VL chain of the clone Fv1E4 is shown in SEQ ID NO: 16. Also, the amino acid sequences of CDR1 to CDR3 of said VL chain are shown in SEQ ID NOs: 17 to 19, respectively. Thus, in the amino acid sequence of VL chain as depicted in SEQ ID NO: 16, the amino acid sequence of the amino acid residues No. 23 to No. 36 corresponds to CDR1 (SEQ ID NO: 17), the amino acid sequence of the amino acid residues No. 52 to No. 58 to CDR2 (SEQ ID NO: 18), and the amino acid sequence of the amino acid residues No. 91 to No. 100 to CDR3 (SEQ ID NO: 19). The nucleotide sequence coding for the amino acid sequence of said VL chain is shown in SEQ ID NO: 20.

(3) Fv1E7 Clone

The amino acid sequence of VH chain of the clone Fv1E7 is shown in SEQ ID NO: 21. Also, the amino acid sequences of CDR1 to CDR3 of said VH chain are shown in SEQ ID NOs: 22 to 24, respectively. Thus, in the amino acid sequence of VH chain as depicted in SEQ ID NO: 21, the amino acid sequence of the amino acid residues No. 30 to No. corresponds to CDR1 (SEQ ID NO: 22), the amino acid sequence of the amino acid residues No. 50 to No. 66 to CDR2 (SEQ ID NO: 23), and the amino acid sequence of the amino acid residues No. 99 to No. 111 to CDR3 (SEQ ID NO: 24). The nucleotide sequence coding for the amino acid sequence of said VH chain is shown in SEQ ID NO: 25.

The amino acid sequence of VL chain of the clone Fv1E7 is shown in SEQ ID NO: 26. Also, the amino acid sequences of CDR1 to CDR3 of said VL chain are shown in SEQ ID NOs: 27 to 29, respectively. Thus, in the amino acid sequence of VL chain as depicted in SEQ ID NO: 26, the amino acid sequence of the amino acid residues No. 23 to No. 33 corresponds to CDR1 (SEQ ID NO: 27), the amino acid sequence of the amino acid residues No. 49 to No. 55 to CDR2 (SEQ ID NO: 28), and the amino acid sequence of the amino acid residues No. 88 to No. 99 to CDR3 (SEQ ID NO: 29). The nucleotide sequence coding for the amino acid sequence of said VL chain is shown in SEQ ID NO: 30.

(4) Fv2A7 Clone

The amino acid sequence of VH chain of the clone Fv2A7 is shown in SEQ ID NO: 31. Also, the amino acid sequences of CDR1 to CDR3 of said VH chain are shown in SEQ ID NOs: 32 to 34, respectively. Thus, in the amino acid sequence of VH chain as depicted in SEQ ID NO: 31, the amino acid sequence of the amino acid residues No. 30 to No. corresponds to CDR1 (SEQ ID NO: 32), the amino acid sequence of the amino acid residues No. 50 to No. 66 to CDR2 (SEQ ID NO: 33), and the amino acid sequence of the amino acid residues No. 99 to No. 112 to CDR3 (SEQ ID NO: 34). The nucleotide sequence coding for the amino acid sequence of said VH chain is shown in SEQ ID NO: 35.

The amino acid sequence of VL chain of the clone Fv2A7 is shown in SEQ ID NO: 36. Also, the amino acid sequences of CDR1 to CDR3 of said VL chain are shown in SEQ ID NOs: 37 to 39, respectively. Thus, in the amino acid sequence of VL chain as depicted in SEQ ID NO: 36, the amino acid sequence of the amino acid residues No. 24 to No. 35 corresponds to CDR1 (SEQ ID NO: 37), the amino acid sequence of the amino acid residues No. 51 to No. 57 to CDR2 (SEQ ID NO: 38), and the amino acid sequence of the amino acid residues No. 90 to No. 98 to CDR3 (SEQ ID NO: 39). The nucleotide sequence coding for the amino acid sequence of said VL chain is shown in SEQ ID NO: 40.

(5) Fv2A8 Clone

The amino acid sequence of VH chain of the clone Fv2A8 is shown in SEQ ID NO: 41. Also, the amino acid sequences of CDR1 to CDR3 of said VH chain are shown in SEQ ID NOs: 42 to 44, respectively. Thus, in the amino acid sequence of VH chain as depicted in SEQ ID NO: 41, the amino acid sequence of the amino acid residues No. 30 to No. corresponds to CDR1 (SEQ ID NO: 42), the amino acid sequence of the amino acid residues No. 50 to No. 68 to CDR2 (SEQ ID NO: 43), and the amino acid sequence of the amino acid residues No. 101 to No. 112 to CDR3 (SEQ ID NO: 44). The nucleotide sequence coding for the amino acid sequence of said VH chain is shown in SEQ ID NO: 45.

The amino acid sequence of VL chain of the clone Fv2A8 is shown in SEQ ID NO: 46. Also, the amino acid sequences of CDR1 to CDR3 of said VL chain are shown in SEQ ID NOs: 47 to 49, respectively. Thus, in the amino acid sequence of VL chain as depicted in SEQ ID NO: 46, the amino acid sequence of the amino acid residues No. 20 to No. 32 corresponds to CDR1 (SEQ ID NO: 47), the amino acid sequence of the amino acid residues No. 48 to No. 54 to CDR2 (SEQ ID NO: 48), and the amino acid sequence of the amino acid residues No. 87 to No. 97 to CDR3 (SEQ ID NO: 49). The nucleotide sequence coding for the amino acid sequence of said VL chain is shown in SEQ ID NO: 50.

(6) Fv2B6 Clone

The amino acid sequence of VH chain of the clone Fv2B6 is shown in SEQ ID NO: 51. Also, the amino acid sequences of CDR1 to CDR3 of said VH chain are shown in SEQ ID NOs: 52 to 54, respectively. Thus, in the amino acid sequence of VH chain as depicted in SEQ ID NO: 51, the amino acid sequence of the amino acid residues No. 30 to No. corresponds to CDR1 (SEQ ID NO: 52), the amino acid sequence of the amino acid residues No. 49 to No. 66 to CDR2 (SEQ ID NO: 53), and the amino acid sequence of the amino acid residues No. 98 to No. 110 to CDR3 (SEQ ID NO: 54). The nucleotide sequence coding for the amino acid sequence of said VH chain is shown in SEQ ID NO: 55.

The amino acid sequence of VL chain of the clone Fv2B6 is shown in SEQ ID NO: 56. Also, the amino acid sequences of CDR1 to CDR3 of said VL chain are shown in SEQ ID NOs: 57 to 59, respectively. Thus, in the amino acid sequence of VL chain as depicted in SEQ ID NO: 56, the amino acid sequence of the amino acid residues No. 23 to No. 36 corresponds to. CDR1 (SEQ ID NO: 57), the amino acid sequence of the amino acid residues No. 52 to No. 58 to CDR2 (SEQ ID NO: 58), and the amino acid sequence of the amino acid residues No. 91 to No. 99 to CDR3 (SEQ ID NO: 59). The nucleotide sequence coding for the amino acid sequence of said VL chain is shown in SEQ ID NO: 60.

(7) B7 Clone

The amino acid sequence of VH chain of the clone B7 is shown in SEQ ID NO: 61. Also, the amino acid sequences of CDR1 to CDR3 of said VH chain are shown in SEQ ID NOs: 62 to 64, respectively. Thus, in the amino acid sequence of VH chain as depicted in SEQ ID NO: 61, the amino acid sequence of the amino acid residues No. 31 to No. corresponds to CDR1 (SEQ ID NO: 62), the amino acid sequence of the amino acid residues No. 50 to No. 66 to CDR2 (SEQ ID NO: 63), and the amino acid sequence of the amino acid residues No. 99 to No. 112 to CDR3 (SEQ ID NO: 64). The nucleotide sequence coding for the amino acid sequence of said VH chain is shown in SEQ ID NO: 65.

The amino acid sequence of VL chain of the clone B7 is shown in SEQ ID NO: 66. Also, the amino acid sequences of CDR1 to CDR3 of said VL chain are shown in SEQ ID NOs: 67 to 69, respectively. Thus, in the amino acid sequence of VL chain as depicted in SEQ ID NO: 66, the amino acid sequence of the amino acid residues No. 23 to No. 33 corresponds to CDR1 (SEQ ID NO: 67), the amino acid sequence of the amino acid residues No. 49 to No. 55 to CDR2 (SEQ ID NO: 68), and the amino acid sequence of the amino acid residues No. 88 to No. 98 to CDR3 (SEQ ID NO: 69). The nucleotide sequence coding for the amino acid sequence of said VL chain is shown in SEQ ID NO: 70.

(8) B6 Clone

The amino acid sequence of VH chain of the clone B6 is shown in SEQ ID NO: 71. Also, the amino acid sequences of CDR1 to CDR3 of said VH chain are shown in SEQ ID NOs: 72 to 74, respectively. Thus, in the amino acid sequence of VH chain as depicted in SEQ ID NO: 71, the amino acid sequence of the amino acid residues No. 31 to No. corresponds to CDR1 (SEQ ID NO: 72), the amino acid sequence of the amino acid residues No. 50 to No. 66 to CDR2 (SEQ ID NO: 73), and the amino acid sequence of the amino acid residues No. 99 to No. 112 to CDR3 (SEQ ID NO: 74). The nucleotide sequence coding for the amino acid sequence of said VH chain is shown in SEQ ID NO: 75.

The amino acid sequence of VL chain of the clone B6 is shown in SEQ ID NO: 76. Also, the amino acid sequences of CDR1 to CDR3 of said VL chain are shown in SEQ ID NOs: 77 to 79, respectively. Thus, in the amino acid sequence of VL chain as depicted in SEQ ID NO: 76, the amino acid sequence of the amino acid residues No. 23 to No. 33 corresponds to CDR1 (SEQ ID NO: 77), the amino acid sequence of the amino acid residues No. 49 to No. 55 to CDR2 (SEQ ID NO: 78), and the amino acid sequence of the amino acid residues No. 88 to No. 98 to CDR3 (SEQ ID NO: 79). The nucleotide sequence coding for the amino acid sequence of said VL chain is shown in SEQ ID NO: 80.

(9) F10 Clone

The amino acid sequence of VH chain of the clone F10 is shown in SEQ ID NO: 81. Also, the amino acid sequences of CDR1 to CDR3 of said VH chain are shown in SEQ ID NOs: 82 to 84, respectively. Thus, in the amino acid sequence of VH chain as depicted in SEQ ID NO: 81, the amino acid sequence of the amino acid residues No. 31 to No. 35 corresponds to CDR1 (SEQ ID NO: 82), the amino acid sequence of the amino acid residues No. 50 to No. 66 to CDR2 (SEQ ID NO: 83), and the amino acid sequence of the amino acid residues No. 99 to No. 114 to CDR3 (SEQ ID NO: 84). The nucleotide sequence coding for the amino acid sequence of said VH chain is shown in SEQ ID NO: 85.

The amino acid sequence of VL chain of the clone F10 is shown in SEQ ID NO: 86. Also, the amino acid sequences of CDR1 to CDR3 of said VL chain are shown in SEQ ID NOs: 87 to 89, respectively. Thus, in the amino acid sequence of VL chain as depicted in SEQ ID NO: 86, the amino acid sequence of the amino acid residues No. 23 to No. 33 corresponds to CDR1 (SEQ ID NO: 87), the amino acid sequence of the amino acid residues No. 49 to No. 55 to CDR2 (SEQ ID NO: 88), and the amino acid sequence of the amino acid residues No. 88 to No. 98 to CDR3 (SEQ ID NO: 89). The nucleotide sequence coding for the amino acid sequence of said VL chain is shown in SEQ ID NO: 90.

(10) D1 Clone

The amino acid sequence of VH chain of the clone D1 is shown in SEQ ID NO: 91. Also, the amino acid sequences of CDR1 to CDR3 of said VH chain are shown in SEQ ID NOs: 92 to 94, respectively. Thus, in the amino acid sequence of VH chain as depicted in SEQ ID NO: 91, the amino acid sequence of the amino acid residues No. 31 to No. 35 corresponds to CDR1 (SEQ ID NO: 92), the amino acid sequence of the amino acid residues No. 50 to No. 66 to CDR2 (SEQ ID NO: 93), and the amino acid sequence of the amino acid residues No. 99 to No. 106 to CDR3 (SEQ ID NO: 94). The nucleotide sequence coding for the amino acid sequence of said VH chain is shown in SEQ ID NO: 95.

The amino acid sequence of VL chain of the clone D1 is shown in SEQ ID NO: 96. Also, the amino acid sequences of CDR1 to CDR3 of said VL chain are shown in SEQ ID NOs: 97 to 99, respectively. Thus, in the amino acid sequence of VL chain as depicted in SEQ ID NO: 96, the amino acid sequence of the amino acid residues No. 23 to No. 33 corresponds to CDR1 (SEQ ID NO: 97), the amino acid sequence of the amino acid residues No. 49 to No. 55 to CDR2 (SEQ ID NO: 98), and the amino acid sequence of the amino acid residues No. 88 to No. 98 to CDR3 (SEQ ID NO: 99). The nucleotide sequence coding for the amino acid sequence of said VL chain is shown in SEQ ID NO: 100.

(11) VLA2 Clone

The amino acid sequence of the clone VLA2 comprising VL chain alone is shown in SEQ ID NO: 101. Also, the amino acid sequences of CDR1 to CDR3 of said VL chain are shown in SEQ ID NOs: 102 to 104, respectively. Thus, in the amino acid sequence of VL chain as depicted in SEQ ID NO: 101, the amino acid sequence of the amino acid residues No. 24 to No. 40 corresponds to CDR1 (SEQ ID NO: 102), the amino acid sequence of the amino acid residues No. 56 to No. 62 to CDR2 (SEQ ID NO: 103), and the amino acid sequence of the amino acid residues No. 95 to No. 103 to CDR3 (SEQ ID NO: 104). The nucleotide sequence coding for the amino acid sequence of said VL chain is shown in SEQ ID NO: 105.

The amino acid sequences and the nucleotide sequences are described above for each of the clones obtained in accordance with the present invention. It may also be possible to use each of the sequences alone or in combination thereof based on the amino acid sequence information for VH chain, VL chain and each CDR 1 to CDR3 as depicted in Sequence Listing.

The antibody and a fragment thereof of the present invention may encompass not only those with VH chain and VL chain and CDRs having the amino acid sequences as depicted in the respective SEQ ID NOs but also mutated polypeptides having said amino acid sequences with partial modification thereof. Thus, the antibody and a fragment thereof of the present invention includes polypeptides that have any of the amino acid sequences as depicted in the respective SEQ ID NOs with one or more amino acid residues therein being substituted, deleted, inserted and/or added and that may serve as a complementarity determining region of H chain or L chain to amyloid β peptide or as a variable region of the H chain or the L chain.

The phrase "with one or more amino acid residues therein being substituted, deleted, inserted and/or added" as used herein means that an amino acid or amino acids is/are substituted, deleted, inserted and/or added in such a number that may ordinarily be introduced by the techniques for preparing mutated proteins known in the art such as site-directed mutagenesis, for instance, in a number of 1 to around 6. Such "mutation" chiefly refers to ones artificially introduced by the techniques for preparing mutated proteins known in the art but may also be obtained as a consequence of isolation and purification of naturally occurring, e.g. in human, polypeptides likewise mutated.

In case that the antibody and a fragment thereof of the present invention is used as a medicament for the treatment, i.e. when administered to human, "mutation" may be done in such an extent that a human-derived structure may be retained or a human does not induce an immune response. For use as a detection device or a diagnosing kit, i.e. when not administered to a human, "mutation" may be done without limitation.

The VH chain and/or VL chain as disclosed by the present invention, though being obtained chiefly in the form of scFv with phage display technique, may not be limited to scFv in principle. For instance, the present invention may also encompass other antibody fragments, including a whole antibody comprising the disclosed VH chain and/or VL chain bound to a constant region of a human immunoglobulin, or Fab, Fab' or F(ab')$_2$ comprising the disclosed VH chain and/or VL chain bound to a portion of a constant region of a human immunoglobulin, or a single chain antibody (scAb) comprising scFv bound to a domain from a constant region of H chain or L chain of a human immunoglobulin, or scFvFc comprising scFv bound to a whole constant region of H chain or L chain of a human immunoglobulin, and the like.

Alternatively, the antibody or a fragment thereof of the present invention may be fused with peptides or other proteins to form a fused antibody or a fragment thereof.

Besides, the antibody or a fragment thereof or the fused antibody or a fragment thereof as described above may also be fused with a high molecular weight modifying agent such as polyethylene glycol to form a modified antibody or a fragment thereof.

For preparing scFv wherein H chain and L chain are linked together via a linker, a peptide linker, e.g. any single chain peptide comprising 10 to 25 amino acid residues, may be used.

The antibody or a fragment thereof, the fused antibody or a fragment thereof, or the modified antibody or a fragment thereof as described above may be utilized as a reagent for detecting Aβ, as an agent for inhibiting Aβ aggregation, or as a medicament for the prophylaxis and treatment of Alzheimer dementia where Aβ is involved, or its diagnostics.

The antibody or a fragment thereof of the present invention may be expressed in a suitable host, e.g. bacteria, yeasts, by introducing genes coding for the VH chain and the VL chain of the respective clones obtained in accordance with the present invention as depicted in SEQ ID NOs: 5, 10, 15, 20, 25, 30, 35, 40, 45, 50, 55, 60, 65, 70, 75, 80, 85, 90, 95, 100, and 105.

Alternatively, the genes of the present invention may be used as a genetic medicament for Alzheimer dementia where Aβ is involved.

The present invention is explained in more detail by means of the following Examples but should not be construed to be limited thereto.

EXAMPLE 1

Construction of Phage Library from Healthy Donors

Phage library was constructed using as a starting material lymphocytes from peripheral blood taken from 20 healthy donors, referring to J. D. Marks et al., *J. Mol. Biol.*, 222: 581-597, 1991. It was estimated that each of the constructed sublibraries VH(γ)–Vκ, VH(γ)–Vλ, VH(μ)–Vκ, and VH(μ)–Vλ exhibited diversity of $1.1\times10^8$, $2.1\times10^8$, $8.4\times10^7$ and $5.3\times10^7$ clones, respectively.

EXAMPLE 2

Panning

Aβ42 peptide (1 μg) dissolved in 0.1 M carbonate buffer, pH 9.6 was added to Cova-link plate (Nunc) activated with 125 μg/ml of DSS 100 μL and the plate was left to stand at 4° C. overnight.

The plate was washed once with PBS containing 0.1% Tween 20 and blocked with 0.5% gelatin for the first selection and with 0.25% BSA for the second selection.

To the plate was added each 100 μL ($5\times10^{11}$ tu/mL) of the antibody phage library derived from healthy donors, a solution of the single chain antibody display phage, divided into either a mixture of VH(γ)–Vκ and VH(γ)–Vλ or a mixture of VH(μ)–Vκ and VH(μ)–Vλ, for reaction at room temperature for 1 hour.

After washing the plate ten times with 0.1% Tween20-PBS, 100 μL glycine buffer (pH 2.2) was added to elute single chain antibody display phages bound to IL-18. After adjusting pH by adding 1 M Tris (hydroxymethyl)-aminomethane-HCl, pH 9.1, the eluted phages were infected to *E. coli* TG1 cells at logarithmic growth phase. The infected TG1 cells were centrifuged at 3,000×g for 10 minutes. After supernatant was removed, the cells were suspended in 200 μL 2×YT culture medium, plated on SOBAG plate (SOB plate containing 2% glucose, 100 μg/ml ampicillin) and then incubated overnight in an incubator at 30° C. The resulting colonies were suspended and recovered in a suitable amount of 2×YT culture medium with a scraper (Costar).

The obtained TG1 solution (50 μL) was inoculated on 30 mL 2×YT culture medium and rescued with a helper phage to prepare a phage library after screening. For each of the phage libraries VH(γ)–Vκ/VH(γ)–Vλ and VH(μ)–Vκ/VH(μ)–Vλ derived from healthy donors, two pannings in total were performed with the plate immobilized with Aβ42 peptide. After the second panning, any clone was extracted arbitrarily from the SOBAG plate. The scFv expression was confirmed, specificity was confirmed by Aβ42 peptide ELISA and a nucleotide sequence was analyzed.

EXAMPLE 3

Aβ42 Peptide ELISA for Screening

For screening the isolated clones, ELISA was performed as described below. Aβ42 peptide was immobilized on an ELISA plate for screening. Each 40 μL/well of Aβ42 peptide (1.25 μg/mL) and a human serum albumin (HSA; 2.5 μg/mL) were placed in an ELISA plate (Nunc) which was left to stand at 4° C. for 16 hours for immobilization. The immobilized plate was added with a PBS solution (400 μL/well) containing 0.5% BSA, 0.5% gelatin and 5% skimmed milk and was left to stand at 4° C. for 2 hours for blocking.

To the plate were added sample solutions (40 μL/well) containing scFv display phage for reaction. The sample solutions were discarded and the plate was washed five times with a washing solution. The plate was reacted with biotin-labeled anti-M13 monoclonal antibody (Pharmacia biotech) and then with anti-mouse IgG antibody labeled with alkaline phosphatase (AP). After washing five times with a washing solution, the plate was added with 50 µL/well of a developing solution of a substrate, i.e. a PBS solution containing 1 g/mL p-nitrophenyl phosphate (Wako) and 10% diethanolamine (Wako), light-shielded, and developed at room temperature to 37° C. for 5 to 10 minutes. Absorbance at 405 nm was measured using Multiplate Autoreader NJ-2001 (Inter Med). As a result, all the clones estimated were confirmed to be specific to Aβ42 peptide.

EXAMPLE 4

Sequence Analysis of Clones

A DNA nucleotide sequence of the isolated clones was determined for scFv gene VH and VL using Dye terminator cycle sequencing FS Ready Reaction kit (Applied Biosystems). As a result of ELISA and sequence analysis, the isolated clones were classified into six variants of scFv and one VL.

EXAMPLE 5

Expression and Purification of Human-derived Anti-Aβ42 Peptide scFv

Plasmid DNAs were recovered from the scFv clones reactive with Aβ42 peptide isolated in Examples 2 and 3 and were used for transfecting *E. coli* HB2151 in conventional manner. The transfected *E. coli* cells were preincubated overnight in 2×YT culture medium containing 2% glucose and 100 µg/mL of ampicillin. A portion of the culture was then transferred to glucose-free 2×YT culture medium, to which IPTG at a final concentration of 1 mM and 100 µg/mL of ampicillin were further added for culture overnight to induce expression of scFv. After completion of culture, the cells were recovered by centrifuge, suspended in PBS containing 1 mM EDTA and left to stand in ice for 30 minutes. Next, the cells were centrifuged at 8,900×g for 30 minutes. Supernatant was recovered and passed through 0.45 µm filter and the filtrate was used as a starting material for purification of scFv from the periplasm fraction.

The thus prepared starting material for purification was purified by affinity purification using an anti-E tag antibody in a conventional manner. After dialysis with PBS, endotoxins were removed with Detoxi-gel (PIERCE) according to the protocol attached thereto. After concentration with Centricon (Amicon) with a cutoff of a molecular weight 10,000, the concentrate was passed through 0.45 µm filter to prepare a purified product.

EXAMPLE 6

Binding Property of Purified scFv to Aβ42 Peptide

A binding property of the purified scFv to Aβ42 peptide was then measured by ELISA. The purified antibody (100 βL) was added to a 96-well plate (NUNC. MAXISORP) with immobilized Aβ42 peptide, which was adjusted to 1.25 µg/mL with PBS for reaction, at 37° C. for 1 hour. After washing five times with 0.05% Tween-PBS (hereinafter also referred to as "PBST"), the plate was reacted with an anti-E tag antibody at 37° C. for 1 hour. After further washing with PBST five times, the plate was reacted with an anti-mouse IgG antibody labeled with alkali phosphatase (AP) at 37° C. for 1 hour. After washing five times with PBST, a developing substrate was added to the plate for stain and absorbance at 405 nm was measured to estimate the binding property. The results are shown in FIG. 1. All the five variants of scFv which could be estimated with sufficient expression were proved to specifically bind to Aβ42 peptide. Although data are not shown, the other scFv, B7, also specifically bound to Aβ42 peptide.

EXAMPLE 7

Analysis of Specificity of Purified scFv

Figure 2:
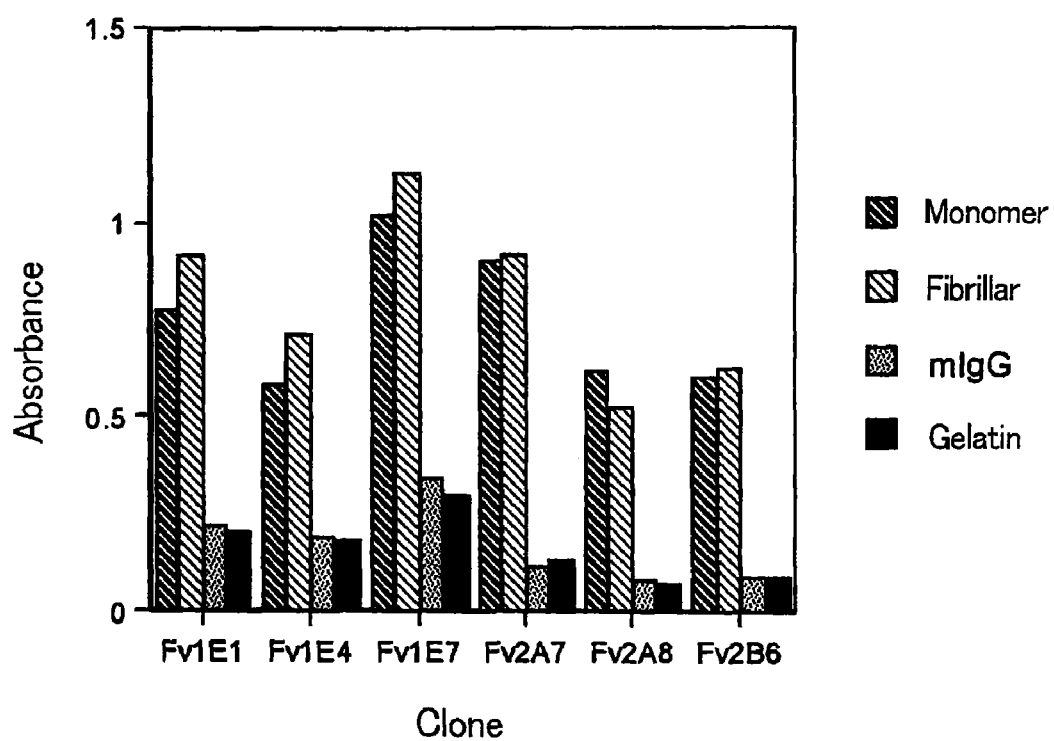
FIG. 2 is a graph showing the results of ELISA where solubility and specificity to fibrillar Aβ42 peptide of scFv from the isolated clones were estimated.

A binding property of scFv to fibrillar Aβ42 peptide was measured by ELISA. The purified scFv (100 µL) from the periplasm fraction of *E. coli* was added to a 96-well plate (NUNC. MAXISORP) with immobilized fibrillar Aβ42 peptide, soluble Aβ42 peptide, being adjusted to 1.25 µg/mL with PBS, 5 µg/mL of mouse IgG and 0.5% gelatin alone for reaction at 37° C. for 1 hour. After washing five times with 0.05% Tween-PBS (hereinafter also referred to as "PEST"), the plate was reacted with a biotin-modified anti-E tag antibody at 37° C. for 1 hour. After further washing with PBST five times, the plate was reacted with streptavidin labeled with alkali phosphatase (AP) at 37° C. for 30 minutes. After washing five times with PEST, a developing substrate was added to the plate for stain and absorbance at 405 nm was measured to estimate the binding property. The results are shown in FIG. 2. All the six variants of scFv estimated were proved to strongly bind to fibrillar Aβ42 peptide as well as soluble Aβ42 peptide.

EXAMPLE 8

Expression and Purification of Human-derived Anti-Aβ42 Peptide VL Chain

Figure 3:
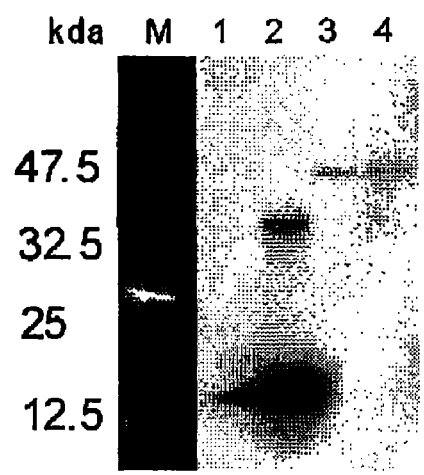
FIG. 3 is a graph showing the results of Western blot analysis to confirm expression of expressed scFv-His6 and VL-D1-D2-His with an anti-His6 antibody.

Among the clones reactive with Aβ42 peptide isolated in Examples 2 and 3, one clone was consisted of JH chain in portion and VL chain. From the DNA of this clone, the VK chain region alone was recloned by PCR to thereby add a recognition site for the restriction enzyme SfiI at 5' end and a recognition site for the restriction enzyme NotI at 3' end. After cleavage with these restriction enzymes and purification on agarose gel electrophoresis, VL chain of this clone was incorporated into pTrc99A–D1+D2-His, an expression vector for expression in the form of a fused protein with D1 and D2 domains of g3 protein from fibrous phages to which end $His_6$ is bound. The resulting expression vector was used to transfect *E. coli* JM83. The transfectant cells were cultured as described in Example 5 and VL–D1–D2-$His_6$ protein was recovered from the periplasm fraction of *E. coli*. After Western blot analysis, expression of the fused protein with a band of 47 Kda as designed was confirmed (FIG. 3).

EXAMPLE 9

Binding Property of VL Chain to Aβ42 Peptide

Figure 4:
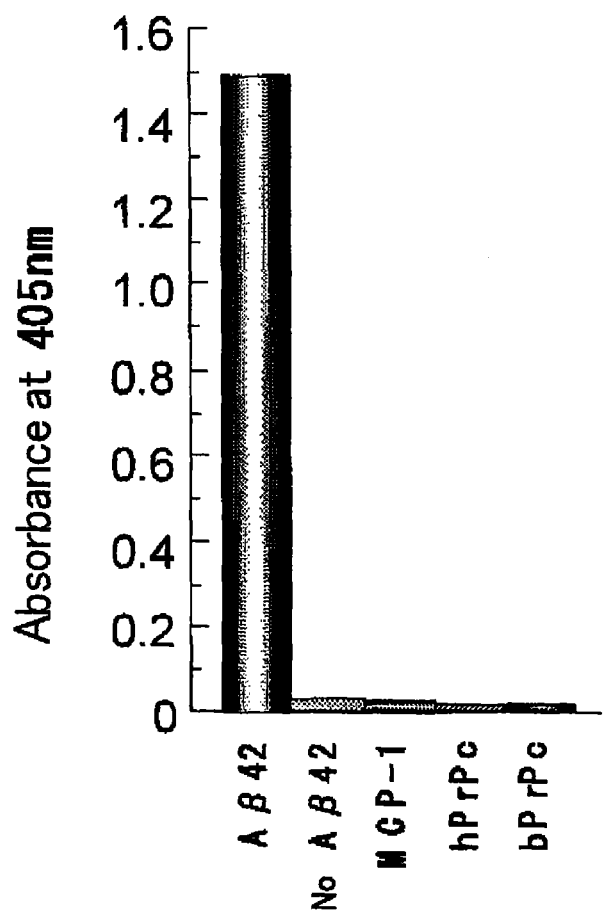
FIG. 4 is a graph showing the results of ELISA where specificity to Aβ42 peptide of VL-D1-D2-His was estimated.

The VL chain (40 µL/well) recovered in Example 8 was added to an ELISA plate and the plate was left to stand at room temperature for 6 hours. After washing once with PBS containing 0.1% Tween 20, the plate was blocked with 0.25% BSA. To the plate were added 100 ng/well of Aβ42 peptide, MCP-1, IL-5, human prion or bovine prion (PrPc102-241 InPro BioTech) for reaction at 37° C. for 1 hour. After washing five times with PBST, the plate was further reacted with secondary antibodies for the respective antigens, i.e. an anti-Aβ42 monoclonal antibody, an anti-MCP-1 monoclonal antibody, an anti-IL-5 monoclonal antibody, and an anti-prion monoclonal antibody. After washing with PBST five times, the plate was reacted with an anti-mouse antibody labeled with alkali phosphatase at 37° C. for 1 hour. After washing five times with PBST, a developing substrate was added to the plate for stain and absorbance at 405 nm was measured to estimate the binding property. The results are shown in FIG. 4. The estimated VL specifically bound to Aβ42 peptide.

EXAMPLE 10

Estimation of Ability of Purified scFv to Inhibit Aβ42 Peptide Aggregation

Figure 5:
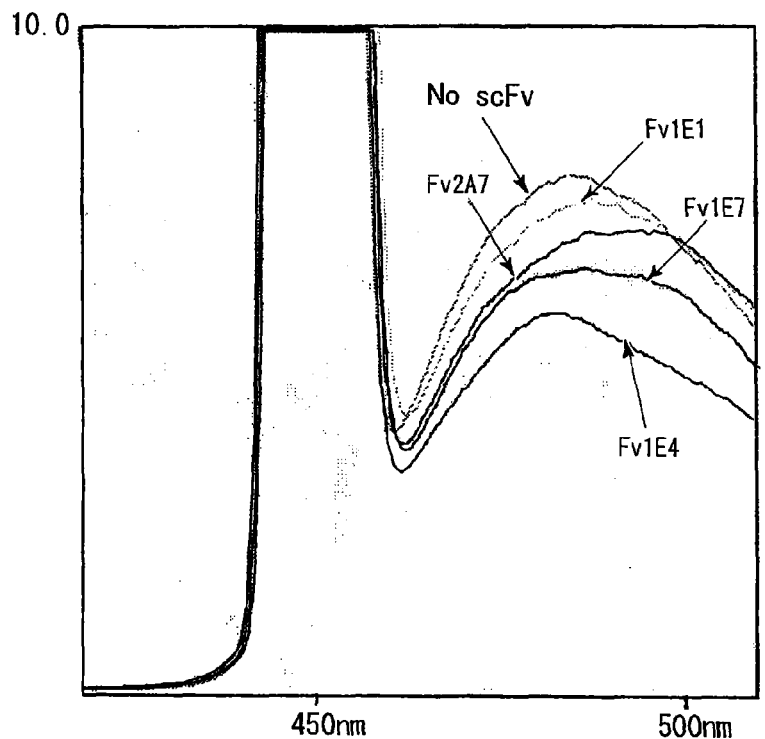
FIG. 5 is a graph showing the results of fluorescent thioflavin test where the activity of purified scFv to inhibit fibrillar amyloid formation of Aβ42 peptide was estimated.

The purified scFv as prepared in Example 5 was used to estimate its ability to inhibit Aβ42 peptide aggregation. Estimation of the inhibitory ability to aggregation was done with fluorescent thioflavin test wherein progress of fibrillar amyloid formation was observed. A sample of the purified scFv at 220 nM was diluted to 4 nM with 0.1 M potassium phosphate buffer, pH6.5, containing 10 μM thioflavin and stirred at room temperature for 2 minutes, at which 1% wt/wt of a seed aggregate, previously sonicated for inhibition of macromolecule formation, was also added simultaneously. Fluorescence at 482 nm for excitation beam of thioflavin dye at 450 nm was measured (Hitachi, F-3000) to estimate formation of aggregates. As a result, all the four clones estimated were proved to inhibit the aggregation (FIG. 5).

EXAMPLE 11

Figure 6:
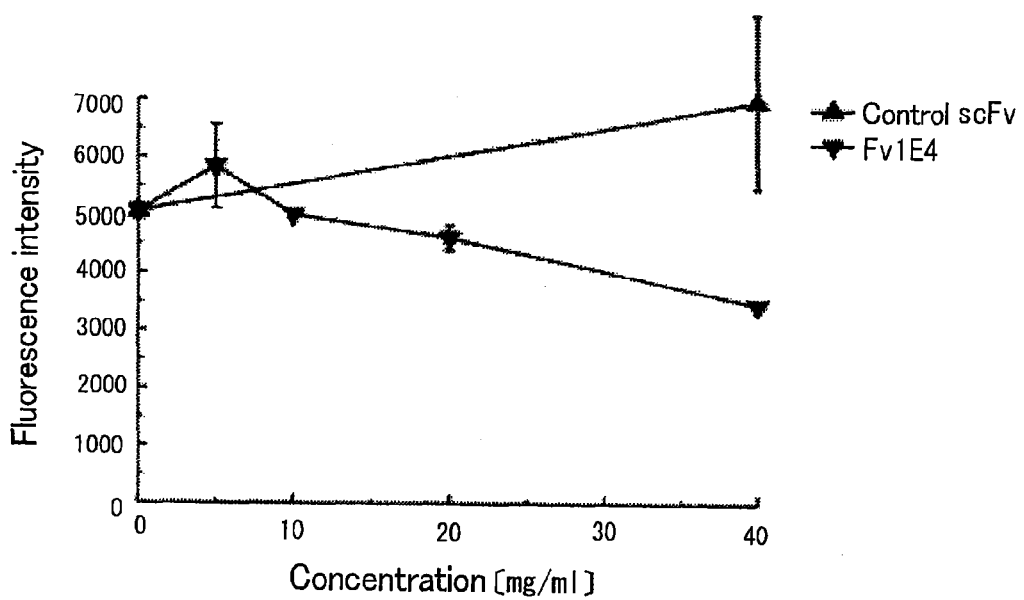
FIG. 6 is a graph showing concentration-dependency of the activity to inhibit aggregation of Aβ42 peptide by purified scFv (Fv1E4).
Figure 7:
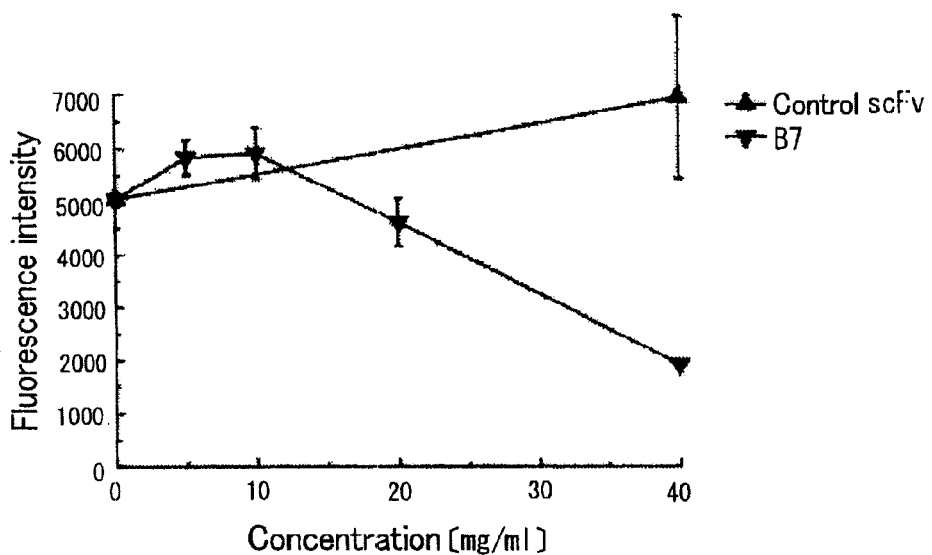
FIG. 7 is a graph showing concentration-dependency of the activity to inhibit aggregation of Aβ42 peptide by purified scFv (B7).

Estimation of Concentration-dependency in Ability of Purified scFv to Inhibit Aβ42 Peptide Aggregation The purified scFv as prepared in Example 5 was used to estimate concentration-dependency in the ability to inhibit Aβ42 peptide aggregation. Estimation of the inhibitory ability to aggregation was done as in Example 10 with fluorescent thioflavin test wherein progress of fibrillar amyloid formation was observed. To 20 μM Aβ42 were added control scFv and the purified scFv, Fv1E4 and B7, at 0-40 μg/ml and the mixture was left to stand at 37° C. for 24 hours. After the concentration of Aβ42 was adjusted to 2 μM, thioflavin T was added at 10 μM and the mixture was stirred at room temperature for 2 minutes. Fluorescence at 482 nm for excitation beam of thioflavin dye at 450 nm was measured (Hitachi, F-3000) to estimate formation of aggregates. As a result, both two clones estimated were proved to inhibit the aggregation in a concentration-dependent manner (FIGS. 6 and 7).

EXAMPLE 12

Binding Property of scFv Display Phage to Fibrillar Aβ42 Peptide

A binding property of scFv display phage to fibrillar Aβ42 peptide was measured by ELISA. Each 40 μL/well of fibrillar Aβ42 peptide and soluble Aβ42 peptide, each adjusted to 50 ng/mL with PBS, and Aβ serum diluted by 1,000 folds were added to an ELISA plate (Nunc) and the plate was left to stand at 4° C. for 6 hours for immobilization. A PBS solution (400 μL/well) containing 0.25% BSA was added to the immobilized ELISA plate and the plate was left to stand at 4° C. overnight for blocking.

Figure 8:
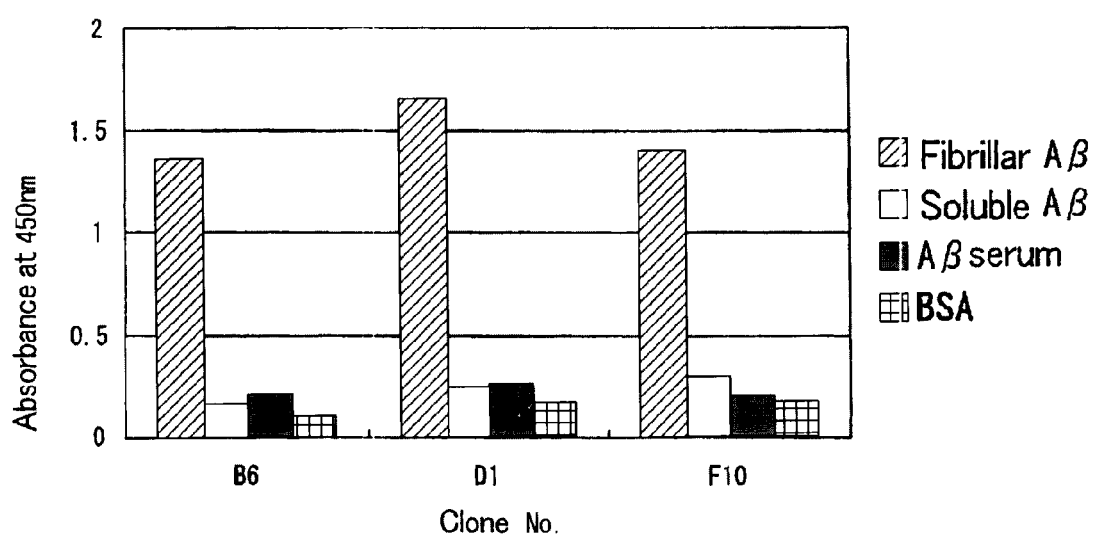
FIG. 8 is a graph showing a binding property of scFv display phages to fibrillar Aβ42 peptide.

To the plate was added a sample solution (40 μL/well) containing scFv display phage for reaction and then the sample solution was discarded and the plate was washed five times with a washing solution. The plate was reacted with an anti-M13 monoclonal antibody (Pharmacia biotech) labeled with biotin and then with an anti-mouse IgG antibody labeled with alkali phosphatase (AP). After washing five times with a washing solution, a solution (50 μL/well) containing a developing substrate, i.e. PBS solution containing 1 g/mL p-nitrophenyl phosphate (Wako) and 10% ethanolamine (Wako), was added to the plate, light-shielded, absorbance at 405 nm was measured using Multiplate Autoreader NJ-2001 (Inter Med). As a result, all the clones estimated were proved to be specific to fibrillar Aβ42 peptide (FIG. 8).

EXAMPLE 13

Binding Property of scFv to Fibrillar Aβ42 Peptide

Figure 9:
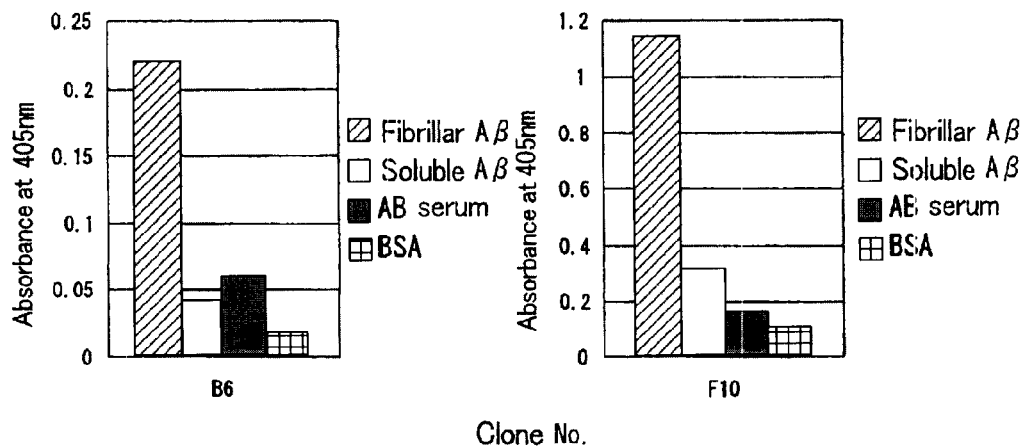
FIG. 9 is a graph showing a binding property of scFv to fibrillar Aβ42 peptide.

A binding property of scFv to fibrillar Aβ42 peptide was measured by ELISA. Each 40 μL/well of sample solutions containing 3 μg/mL of scFv purified as described in Example 5 was added to the plate as described in Example 12 for reaction. The sample solutions were discarded and the plate was washed five times with a washing solution. The plate was reacted with an anti-Etag mAb (1:1000) and then with a goat anti-mouse IgG (1:1000) labeled with alkali phosphatase. The treatment with a solution containing a developing substrate and the measurement as described in Example 12 were repeated. As a result, the B6 and F10 clones estimated were proved to be specific to fibrillar A342 peptide (FIG. 9).

EXAMPLE 14

Estimation of Ability of Purified scFv to Inhibit Aβ42 Peptide Aggregation

Figure 10:
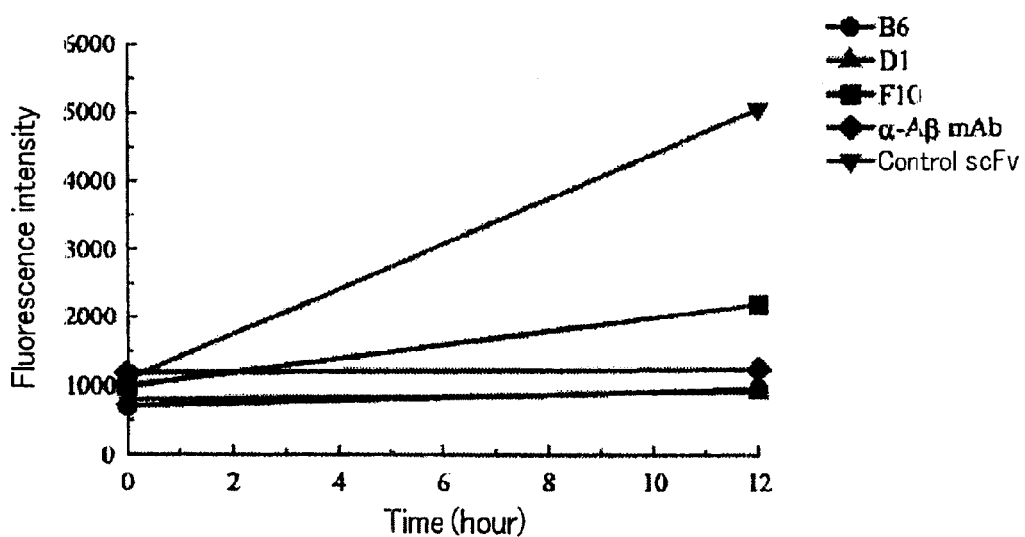
FIG. 10 is a graph showing the results of fluorescent thioflavin test where the activity of purified scFv to inhibit fibrillar amyloid formation of Aβ42 peptide was estimated.

The purified scFv as prepared in Example 13 was used to estimate its ability to inhibit Aβ42 peptide aggregation. Estimation of the inhibitory ability to aggregation was done with fluorescent thioflavin test wherein progress of fibrillar amyloid formation was observed. To a sample was added scFv at a final concentration of 40 μg/ml and the mixture was left to stand. At each fixed time, the sample was collected to adjust a concentration of Aβ to 2 μM, added with thioflavin T at 10 μM and left to stand at room temperature for 2 minutes. Fluorescence at 482 nm for excitation beam of thioflavin dye at 450 nm was measured (Hitachi, F-3000) to estimate formation of aggregates with passage of time. As a result, all the three clones estimated were proved to inhibit the aggregation (FIG. 10).

EXAMPLE 15

Figure 11:
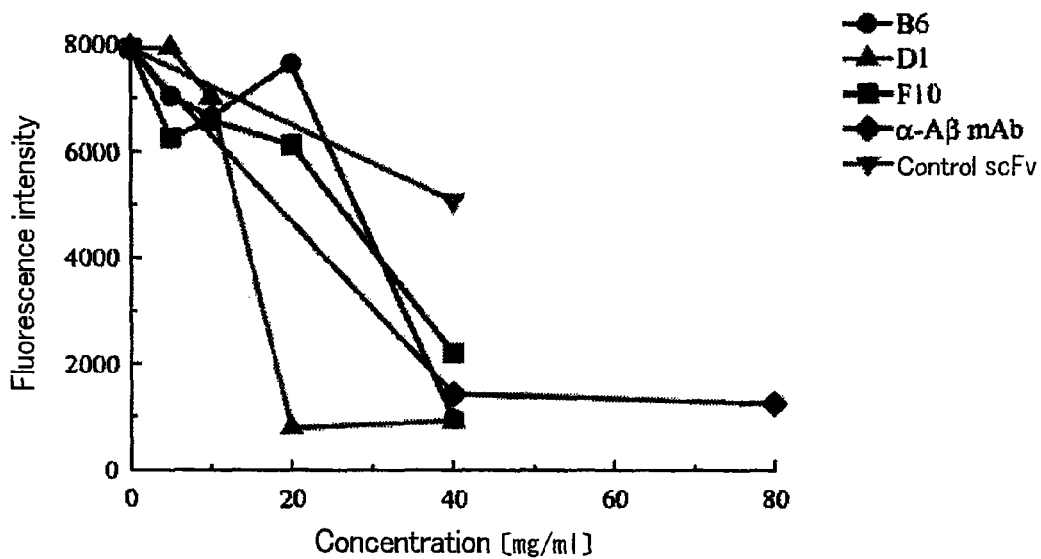
FIG. 11 is a graph showing concentration-dependency of the activity to inhibit aggregation of Aβ42 peptide by purified scFv.

Estimation of Concentration-dependency in Ability of Purified scFv to Inhibit Aβ42 Peptide Aggregation The purified scFv as prepared in Example 13 was used to estimate concentration-dependency in the ability to inhibit Aβ42 peptide aggregation. Estimation of the inhibitory ability to aggregation was done as in Example 14 with fluorescent thioflavin test wherein progress of fibrillar amyloid formation was observed. To 20 μM Aβ42 were added control scFv and the purified scFv at a final concentration of 0-40 μg/ml and the mixture was left to stand at 37° C. for 24 hours. After the concentration of Aβ42 was adjusted to 2 μM, thioflavin T was added at 10 μM and the mixture was stirred at room temperature for 2 minutes. Fluorescence at 482 nm for excitation beam of thioflavin dye at 450 nm was measured (Hitachi, F-3000) to estimate formation of aggregates. As a result, the three clones estimated were proved to inhibit the aggregation in a concentration-dependent manner (FIG. 11).

EXAMPLE 16

Expression and Preparation of tat Peptide-fused Human-Derived Anti-Aβ42 Peptide VL Chain To the Aβ42 peptide specific VL chain gene constructed in Example 8 was added at its 5' end HIV tat peptide sequence (Met Gly Tyr Gly Arg Lys Lys Arg Arg Gln Arg Arg Arg Gly) (SEQ ID NO: 106) by PCR and was incorporated into pET-29b vector (Novagen) with the restriction enzyme sites NdeI and NotI. After transfection into *E. coli* BL21 (DE3) star, the tat-VL chain was expressed as an inclusion body by IPTG induction. The cells were collected, sonicated and centrifuged and the supernatant was removed. Insoluble fractions were solubilized with 6 N guanidine hydrochloride. The obtained solubilized fractions were applied to Ni-NTA column in the presence of 6 N guanidine hydrochloride. After washing the column, proteins bound to the column were eluted with imidazole to provide a fraction of purified tat-VL chain, which was subjected to refolding process by step-wise dialysis as described below. The fraction was adjusted with a solution containing 50 mM Tris-HCl (pH 8.0), 10 mM β-ME, 1 mM EDTA, 200 mM NaCl and 6 M Gdn HCl to prepare a 7.5 μM tat-VL chain solution which was dialyzed with the same solution excluding β-ME for 2 hours. The fraction was further dialyzed with 6 M Gdn HCl for 3 hours, with 3 M Gdn HCl for 6 hours, with 2 M Gdn HCl for 12 hours, with 1 M Gdn HCl/375 μM GSSG/200 mM L-Arginine for 12 hours, with 0.5 M Gdn HCl/375 μM GSSG/200 mM L-Arginine for 12 hours, and with PBS for 12 hours to prepare a tat-VL chain finally in a refolded form.

EXAMPLE 17

Figure 12:
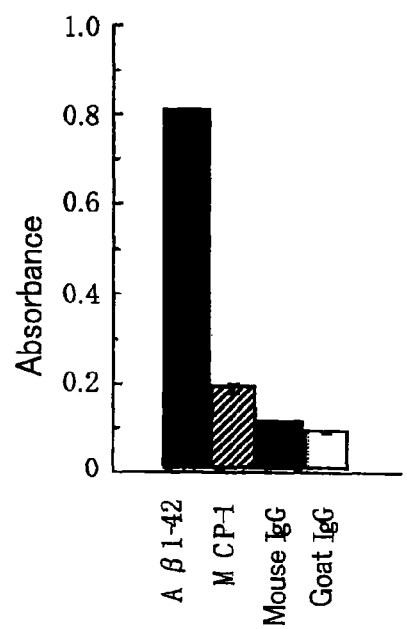
FIG. 12 is a graph showing a binding property of purified tat peptide-fused VL chain to Aβ42 peptide.

Estimation of Binding Property of tat Peptide-fused VL Chain to Aβ42 Peptide The tat peptide-fused VL chain (40 μL/well) recovered in Example 16 was added to an ELISA plate and the plate was left to stand at 4° C. for 12 hours. After washing once with PBS containing 0.1% tween, the plate was blocked with 0.5% gelatin. To the plate were added 100 ng/well of Aβ42 peptide, MCP-1, mouse IgG or goat IgG for reaction at 37° C. for 1 hour. After washing five times with PBST, the plate was further reacted with secondary antibodies for the respective antigens, i.e. an anti-Aβ42 monoclonal antibody, an anti-MCP-1 monoclonal antibody and an anti-goat IgG antibody, with the exception of mouse IgG which was used as it was without washing. After washing with PBST five times, the plate was reacted with an anti-mouse antibody labeled with alkali phosphatase at 37° C. for 1 hour. After washing five times with PBST, a developing substrate was added to the plate for stain and absorbance at 405 nm was measured to estimate the binding property. The results are shown in FIG. 12. The purified tat peptide-fused VL as estimated specifically bound to Aβ42 peptide.

EXAMPLE 18

Figure 13:
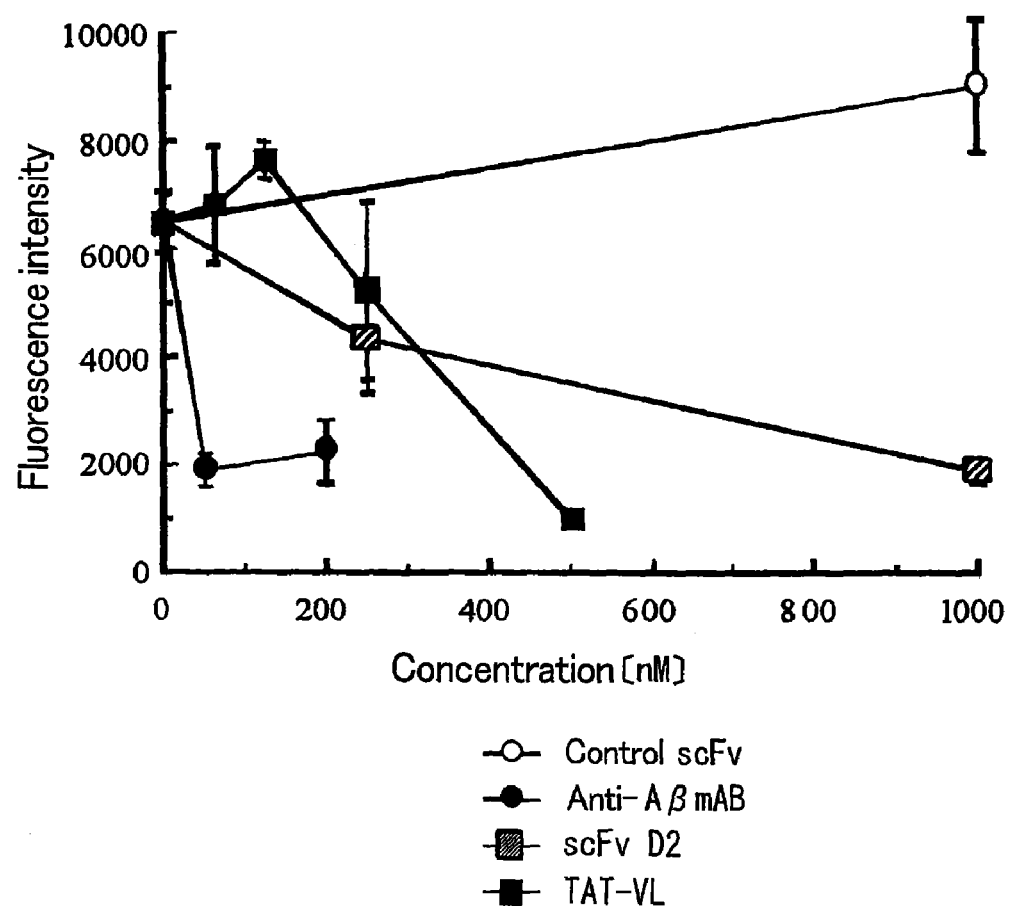
FIG. 13 is a graph showing concentration-dependency of the activity to inhibit aggregation of Aβ42 peptide by purified tat peptide-fused VL chain.

Estimation of Ability of tat Peptide-fused VL Chain to Inhibit Aβ42 Peptide Aggregation The purified tat peptide-fused VL chain as prepared in Example 16 was used to estimate its ability to inhibit Aβ42 peptide aggregation. Estimation of the inhibitory ability to aggregation was done with fluorescent thioflavin test wherein progress of fibrillar amyloid formation was observed as described in Example 10. As a result, the purified tat peptide-fused VL chain estimated was proved to inhibit the aggregation (FIG. 13).

---

---

The invention claimed is:

1. An isolated polynucleotide that encodes a human anti-amyloid β peptide 1-42 (Aβ42) antibody or antigen binding fragment thereof, wherein the antibody or antigen binding fragment comprises the heavy chain CDRs 1-3 of SEQ ID NOs: 72-74, respectively, and the light chain CDRs 1-3 of SEQ ID NOs: 77-79, respectively.

2. A recombinant expression vector comprising the isolated polynucleotide according to claim 1.

3. An isolated host cell comprising the recombinant expression vector of claim 2.

4. A method for producing a human anti-Aβ42 antibody or antigen binding fragment thereof comprising culturing the isolated host cell of claim 3 and recovering the human anti-Aβ42 antibody or antigen-binding fragment thereof produced by the host cell.

5. A composition comprising the isolated polynucleotide according to claim 1.

6. The isolated polynucleotide according to claim 1, wherein the polynucleotide encodes the H chain variable region amino acid sequence of SEQ ID NO: 71 and the L chain variable region amino acid sequence of SEQ ID NO: 76.

7. The isolated polynucleotide according to claim 1, wherein said Aβ42 is fibrillar Aβ42.

8. The isolated polynucleotide according to claim 1, wherein said antigen-binding fragment of the antibody is Fab, Fab', F(ab')$_2$, scAb, or scFv-Fc.

9. An isolated polynucleotide coding for a human anti-amyloid β peptide 1-42 (Aβ42) antibody or an antigen binding fragment of the antibody, wherein the antibody or antigen binding fragment comprises:
   a) a heavy chain variable region comprising CDRs 1-3 of SEQ ID NO: 72-74, and
   b) a light chain variable region fragment of a human anti-Aβ42 antibody.

10. A recombinant expression vector comprising the isolated polynucleotide according to claim 9.

11. An isolated host cell comprising the recombinant expression vector of claim 10.

12. A method for producing a human anti-Aβ42 antibody or antigen binding fragment thereof comprising culturing the isolated host cell of claim 11 and recovering the human anti-Aβ42 antibody or antigen binding fragment thereof produced by the host cell.

13. A composition comprising the isolated polynucleotide according to claim 9.

14. The isolated polynucleotide according to claim 9, wherein said Aβ42 is fibrillar Aβ42.

15. The isolated polynucleotide according to claim 9, wherein said antigen binding fragment of the antibody is Fab, Fab', F(ab')$_2$, scAb, or scFv-Fc.

* * * * *

UNITED STATES PATENT AND TRADEMARK OFFICE
CERTIFICATE OF CORRECTION

PATENT NO.          : 8,222,002 B2
APPLICATION NO.     : 12/792064
DATED               : July 17, 2012
INVENTOR(S)         : Kazuhisa Sugimura et al.

It is certified that error appears in the above-identified patent and that said Letters Patent is hereby corrected as shown below:

On the title page, Item (73), the Assignee should read:

--(73) Assignee: Juridical Foundation The Chemo-Sero-Therapeutic Research Institute, Kumamoto-shi (JP)--

Signed and Sealed this
Eighteenth Day of September, 2012

David J. Kappos
*Director of the United States Patent and Trademark Office*